United States Patent
Claussenelias et al.

(10) Patent No.: US 11,514,061 B2
(45) Date of Patent: *Nov. 29, 2022

(54) HEALTHCARE PROVIDER SEARCH BASED ON EXPERIENCE

(71) Applicant: Healthgrades Marketplace, LLC, Fort Mill, SC (US)

(72) Inventors: Michel Claussenelias, Denver, CO (US); William N. Bell, Westminster, CO (US)

(73) Assignee: HEALTHGRADES MARKETPLACE, LLC, Fort Mill, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/114,051

(22) Filed: Dec. 7, 2020

(65) Prior Publication Data

US 2021/0209119 A1 Jul. 8, 2021

Related U.S. Application Data

(63) Continuation of application No. 14/675,345, filed on Mar. 31, 2015, now Pat. No. 10,977,254.

(Continued)

(51) Int. Cl.
*G06F 16/2457* (2019.01)
*G06F 16/951* (2019.01)
(Continued)

(52) U.S. Cl.
CPC ...... *G06F 16/24578* (2019.01); *G06F 16/951* (2019.01); *G06F 16/953* (2019.01); *G16H 70/00* (2018.01); *G16H 40/67* (2018.01)

(58) Field of Classification Search
CPC ............. G06F 16/24578; G06F 16/951; G06F 16/953; G16H 70/00; G16H 40/67
(Continued)

(56) References Cited

U.S. PATENT DOCUMENTS 5,560,005 A * 9/1996 Hoover ................... G06F 16/27
6,735,569 B1 * 5/2004 Wizig ................ G06Q 10/1057
705/2

(Continued)

*Primary Examiner* — Mark E Hershley
(74) *Attorney, Agent, or Firm* — Seyfarth Shaw LLP

(57) ABSTRACT

The embodiments of the present application relate to providing a distributed network-based system that allows users to search for potential healthcare providers that satisfy certain criteria and to dynamically identify healthcare providers that best meet a user's particular needs as defined by each specific search. In embodiments, the system creates experience score for each particular provider who matches the search criteria. The experience score is dynamically determined based on the type of search that is performed (e.g., search by specialty or search by condition or procedure), the query terms used in the search, and other factors including for example, the medical specialty/specialties the provider practices relative to the search performed, evidence the provider treats a condition and/or performs a procedure that matches the consumer's search, patient volume for the searched condition or procedure, total volume of patients, board certification(s) relevant to searched performed, disciplinary action information, malpractice claims history, and degree level attained by the healthcare provider. In other embodiments, the system dynamically ranks healthcare providers within a search results list from best choice to worst choice based on several factors including, for example, the type of search, the query terms used in the search, the quantity of providers who match the query, the locations of the providers who match the query, and the quality and other characteristics of providers who match the search query.

13 Claims, 12 Drawing Sheets

Related U.S. Application Data

(60) Provisional application No. 61/973,777, filed on Apr. 1, 2014.

(51) Int. Cl.
    *G16H 70/00*     (2018.01)
    *G06F 16/953*     (2019.01)
    *G16H 40/67*     (2018.01)

(58) Field of Classification Search
    USPC ........................................................ 707/723
    See application file for complete search history.

(56) References Cited

U.S. PATENT DOCUMENTS

| | | | | |
|---|---|---|---|---|
| 8,073,731 | B1* | 12/2011 | Rajasenan | G06Q 10/06398 705/7.42 |
| 8,103,524 | B1* | 1/2012 | Rogers | G16H 70/00 705/2 |
| 8,655,478 | B2* | 2/2014 | Fukuda | B24B 53/017 700/13 |
| 2001/0056359 | A1* | 12/2001 | Abreu | A61B 5/4848 705/3 |
| 2004/0254816 | A1* | 12/2004 | Myers | G16H 40/20 705/2 |
| 2006/0161456 | A1* | 7/2006 | Baker | G16Z 99/00 705/2 |
| 2006/0293923 | A1* | 12/2006 | Farris | G16H 70/00 707/999.102 |
| 2007/0156455 | A1* | 7/2007 | Tarino | G06Q 10/00 705/2 |
| 2007/0185732 | A1* | 8/2007 | Hicks | G16H 15/00 705/2 |
| 2007/0192144 | A1* | 8/2007 | Hauer | G06Q 30/0283 705/400 |
| 2007/0250352 | A1* | 10/2007 | Tawil | G16H 10/20 600/300 |
| 2007/0265883 | A1* | 11/2007 | Farris | G16H 40/20 705/3 |
| 2008/0071578 | A1* | 3/2008 | Herz | G16H 10/60 705/311 |
| 2008/0154648 | A1* | 6/2008 | Babyak | G06Q 40/08 705/4 |
| 2008/0154759 | A1* | 6/2008 | Babyak | G06Q 10/10 705/35 |
| 2008/0177994 | A1* | 7/2008 | Mayer | G06F 16/00 709/224 |
| 2008/0312963 | A1* | 12/2008 | Reiner | G06Q 10/06398 705/7.42 |
| 2009/0164252 | A1* | 6/2009 | Morris | G16H 10/60 705/3 |
| 2009/0254971 | A1* | 10/2009 | Herz | G06Q 10/10 726/1 |
| 2009/0328138 | A1* | 12/2009 | Lee | G06Q 10/10 726/1 |
| 2010/0145922 | A1* | 6/2010 | Yoon | G06F 16/9535 707/706 |
| 2010/0217768 | A1* | 8/2010 | Yu | G16H 70/00 707/E17.069 |
| 2010/0228564 | A1* | 9/2010 | Kharraz Tavakol | G16Z 99/00 705/317 |
| 2010/0235295 | A1* | 9/2010 | Zides | G06Q 30/0282 705/347 |
| 2011/0009707 | A1* | 1/2011 | Kaundinya | G16H 40/67 600/300 |
| 2011/0077973 | A1* | 3/2011 | Breitenstein | G06F 3/0484 705/3 |
| 2011/0125527 | A1* | 5/2011 | Nair | G16H 50/70 705/3 |
| 2011/0125528 | A1* | 5/2011 | Padate | G16H 10/60 705/3 |
| 2011/0246231 | A1* | 10/2011 | Sie | G16H 10/60 715/764 |
| 2011/0251848 | A1* | 10/2011 | Alameddine | G16H 10/60 705/5 |
| 2012/0123792 | A1* | 5/2012 | Klein | G16H 10/60 705/2 |
| 2012/0136678 | A1* | 5/2012 | Steinberg | G06Q 30/02 705/3 |
| 2012/0179002 | A1* | 7/2012 | Brunetti | G16H 20/00 600/300 |
| 2012/0310661 | A1* | 12/2012 | Greene | G06Q 10/087 705/2 |
| 2013/0096937 | A1* | 4/2013 | Campbell | G16H 40/20 705/2 |
| 2013/0103423 | A1* | 4/2013 | Kim | G16H 80/00 705/3 |
| 2013/0110532 | A1* | 5/2013 | Upadhyayula | G06Q 10/10 705/2 |
| 2013/0290351 | A1* | 10/2013 | Haga | G06F 16/24578 707/749 |
| 2013/0325509 | A1* | 12/2013 | McCarrick | G16H 70/00 705/2 |
| 2014/0081667 | A1* | 3/2014 | Joao | G16H 40/63 705/3 |
| 2014/0081898 | A1* | 3/2014 | Saigal | G06N 5/048 706/52 |
| 2014/0114674 | A1* | 4/2014 | Krughoff | G06Q 10/10 705/2 |
| 2014/0280055 | A1* | 9/2014 | Chang | G06F 16/9038 707/722 |
| 2014/0331295 | A1* | 11/2014 | Kumar | H04L 63/0807 726/6 |
| 2015/0187032 | A1* | 7/2015 | Mirza | G06Q 30/04 705/311 |
| 2015/0221046 | A1* | 8/2015 | Roy | G06Q 50/00 705/2 |
| 2015/0254416 | A1* | 9/2015 | Shih | G16H 80/00 705/2 |

\* cited by examiner

HEALTHCARE PROVIDER SEARCH BASED ON EXPERIENCE

CROSS REFERENCE TO RELATED APPLICATIONS

This application claims the benefit of U.S. Provisional Patent Application No. 61/973,777 filed on Apr. 1, 2014, entitled "HEALTHCARE PROVIDER SEARCH BASED ON EXPERIENCE" which is incorporated herein by reference it its entirety.

BACKGROUND

Individuals generally try to learn as much information as possible about particular healthcare providers, such as physicians, before selecting a provider for healthcare services. The Internet has become a good source of information for patients to learn about potential healthcare providers. However, one well-recognized problem with the Internet is that the consumer often cannot determine the veracity of the information which is revealed through a search. Further, since the information about healthcare providers on the Internet is often provided by the healthcare providers themselves, this information may not be updated on a regular basis and/or may contain inaccurate or incomplete information. Even further, there is so much information about so many healthcare providers available on the web, it is often difficult, if not impossible, for individuals to sort through the vast amount of information to identify the best healthcare provider to meet his or her needs, particularly because the determination of which providers are best and the ranking of healthcare providers from best to worst depends on a variety of factors that may or may not be relevant to any particular search.

It is with respect to these and other general considerations that embodiments disclosed herein have been made. Also, although relatively specific problems may be discussed, it should be understood that the embodiments should not be limited to solving the specific problems identified in the background or elsewhere in this disclosure.

SUMMARY

In general, the embodiments of the present application relate to providing a distributed network-based business that allows users to locate potential healthcare providers that satisfy certain criteria and to dynamically identify healthcare providers that best meet a user's particular needs as defined by each specific search. In embodiments, a user (e.g., a potential patient, an existing patient or some other individual) may access a webpage or website that provides the user access to a database of healthcare provider information. The website provides the user with the ability to search for a healthcare provider based on various items, including, but not limited to, information associated with actual experiences of the healthcare provider. In embodiments, this actual experience relates to information gleaned from actual insurance claims. These claims relate to claims for reimbursement by healthcare providers that detail the actual service(s) performed on given dates for specific patients and are described/coded by standard taxonomy. Such actual claim information provides another level of veracity to statements made by the healthcare providers themselves. The actual experience information may also include self-reported information gathered from the healthcare providers themselves about their specialties, conditions they have treated, and procedures they have performed. Additionally, actual experience information may include training information about a healthcare provider's education and training as it relates to their specialties, conditions they have treated, and procedures they have performed.

The company maintaining the website (hereinafter, "the company") compiles the criteria and provides a results list of healthcare providers satisfying such criteria. For example, a company website which provides such information and services is www.HealthGrades.com, provided by HealthGrades, Inc. From this results list, a client may access a provider profile using the information in the database.

In essence, the profile contains at least two sections. First, there is a section pertaining to the personal information of the healthcare provider. This section permits healthcare providers to input the desired breadth and depth of the personal information about themselves. This personal information may include age, gender, medical school, graduation date, internships, fellowships, publications, current standing, languages spoken, medical philosophy, hobbies, etc. In other embodiments, another party, such as HealthGrades, may input information in this section as well. For instance, another party would most likely add board certification information and disciplinary action information or links to such actions if any existed. The second section pertains to the expertise and is based on the provider's actual experience. This section provides information relating to the provider's area(s) of specialty, education, training, the conditions treated by the provider, and the procedures performed by the provider. The information relating to actual procedures performed and conditions treated comes from the healthcare provider and/or from insurance companies. The information from the insurance companies includes claim information related to actual claims made for healthcare services rendered. In some embodiments, the procedures performed and conditions treated are compiled from sources including indications from a healthcare provider and indications from claims information. As such, a single condition or procedure identified in a search potentially has multiple levels of veracity applied to it: (1) Has the provider indicated they have experience with the condition or procedure (Yes/No)? (2) Does the claims information further substantiate the healthcare provider has experience with the condition or procedure (Yes/No)? (3) To what degree (percentile comparison of volumes against other providers in terms of patient volumes for the condition or procedure) does the healthcare provider have experience with the condition or procedure?

In embodiments, the expertise section includes an experience score for each particular provider that is dynamically determined based on the type of search that is performed (e.g., search by specialty or search by condition or procedure), the query terms used in the search, and other factors including for example, the medical specialty/specialties the provider practices relative to the search performed, evidence the provider treats a condition and/or performs a procedure that matches the consumer's search, patient volume for the searched condition or procedure, total volume of patients the provider has seen over a certain period of time, whether the provider has board certification(s) relevant to searched performed, disciplinary action information including board actions, sanctions, and malpractice claims history, and degree level attained by the healthcare provider.

In embodiments, searches for providers by a user may be performed from within the website of the company, while other embodiments involve the use search engines external to the website (e.g., Google, Bing, Yahoo, etc.). Some embodiments relate to searches for human healthcare providers, while others relate to searches for hospitals or other types of treatment facilities. While some embodiments relate to searches performed on servers separate from insurance company servers, other embodiments may include searching on such insurance company websites and servers.

As discussed herein, an aspect of a particular embodiment relates to a database of healthcare provider-related information, wherefrom data is gathered and compiled into the form of a profile and is made available to users. Such profiles contain different types of verified information for each healthcare provider within the database. In an exemplary embodiment, in response to a search query for a particular healthcare provider name conducted using a search engine external to the company website, the user receives a web-based "profile" of a selected healthcare provider matching, or closely matching, the entered search terms. A profile lists detailed information potentially available about that healthcare provider which may be obtained in the form of a profile or other displayable content. One embodiment of the invention provides for a standard profile, which provides the healthcare provider's specialty and general location information (city/state) and provides a hyperlink for the user to get more information on that healthcare provider. The other information may be verified in some manner, such as by the company or by some other independent third party. Such verified information may comprise board certifications, disciplinary action(s), if any, education information, years since medical school, etc. In an embodiment, the profile may also include a patient-provided information section, including patient experience surveys completed by patients of the healthcare provider and a place where users accessing the profile may share their experiences with the healthcare provider.

An aspect of a particular embodiment relates to the different levels of verified information available in each provider's profile, in which such information may include: (1) a provider-verified section including information from the provider that he or she feels will help a user choose the provider; (2) a third party-verified section including information received from third parties, such as board certifications, medical school, internship, residency, fellowship, licensure information, disciplinary action(s), if any, malpractice claims, if any, etc.; and (3) a patient-provided information section, including patient experience survey responses by patients of the healthcare provider relating their past experiences with the healthcare provider and/or with the healthcare provider's practice.

In other embodiments, the distributed network-based system and website of the present application relates generally to how this verified healthcare provider information may be accessed by users using the search capabilities provided by the company's webpage. In one embodiment, a user receives a profile of a healthcare provider following a search query by name for a particular healthcare provider. In other embodiments, such as those involving search criteria limited to a healthcare provider with a particular medical specialty, or experience with treating a condition or performing a procedure, a user will be presented with a list of healthcare provider names with hyperlinks to those healthcare provider's individual profiles. The providers are ranked within the search results according to how well they match the search terms used in the search query.

In still other embodiments, the system described in the present application dynamically ranks healthcare providers within a results list from best choice to worst choice based on several factors including, for example, the type of search (e.g., search by specialty or search by condition or procedure) run, the query terms used in the search, the quantity of providers who match the query, the locations of the providers who match the query, and the quality and other characteristics of providers who match the search query. More specifically, the system calculates a total boost score for each provider who matches the search terms and uses the total boost score to rank providers within the results list. The total boost score determines the relevancy of healthcare provider listings by applying multiple factors based on the consumer's search criteria (e.g., medical specialty, search radius, etc.) and information detected about the providers who match this criteria. The total boost score is based upon factors including, for example: distance between the healthcare provider office and the selected location; degree level attained by the healthcare provider; malpractice claims filed; the presence of malpractice judgments or medical board sanctions; sanctions levied or other board actions against the healthcare provider; patient experience satisfaction score and survey volumes; healthcare provider board certification status; volume of patients that provider has diagnosed/treated in relation to the condition or procedure as indicated through claims volumes; volume of claims related to the conditions treated or procedures performed by the healthcare provider; the volume of conditions or procedures with which the healthcare provider has verified having experience; conditions and procedures the healthcare provider has verified they have experience in treating and performing and what healthcare providers are trained to treat and perform based upon their medical specializations; the relationship between searched conditions or procedures and claims involving related conditions or procedures; the provider's total patient volume for their practice in comparison to other provider practices within the same medical specialty; and the quality of the provider's affiliated hospitals as they relate to the search performed.

The various embodiments of the present application may be implemented as a computer process, a computing system or as an article of manufacture, such as a computer program product or computer-readable media. The computer program product may be a computer storage media that is readable by a computer system and is encoding a computer program of instructions for executing a computer process.

These and various other features, as well as advantages, which characterize the present invention, will be apparent from a reading of the following detailed description and a review of the associated drawings. This summary is provided to introduce a selection of concepts in a simplified form that are further described below in the Detailed Description. This Summary is not intended to identify key or essential features of the claimed subject matter, nor is it intended to be used in any way as to limit the scope of the claimed subject matter.

Figure 3A:
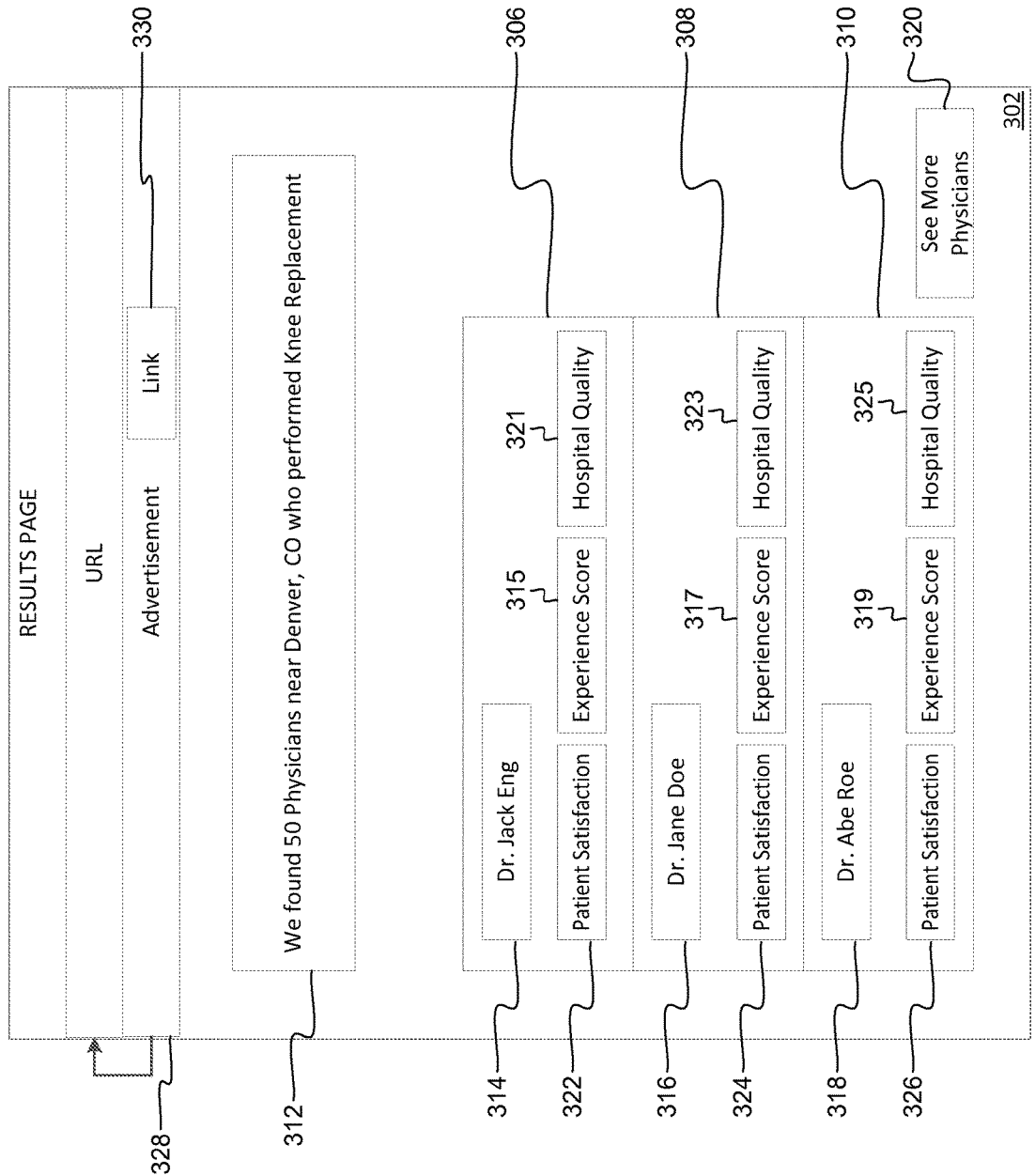
FIG. 3A illustrates search results for a physician "by procedure" search using the network environment of FIG. 1 and the search page of FIG. 2, in accordance with an embodiment of the present application.
Figure 3B:
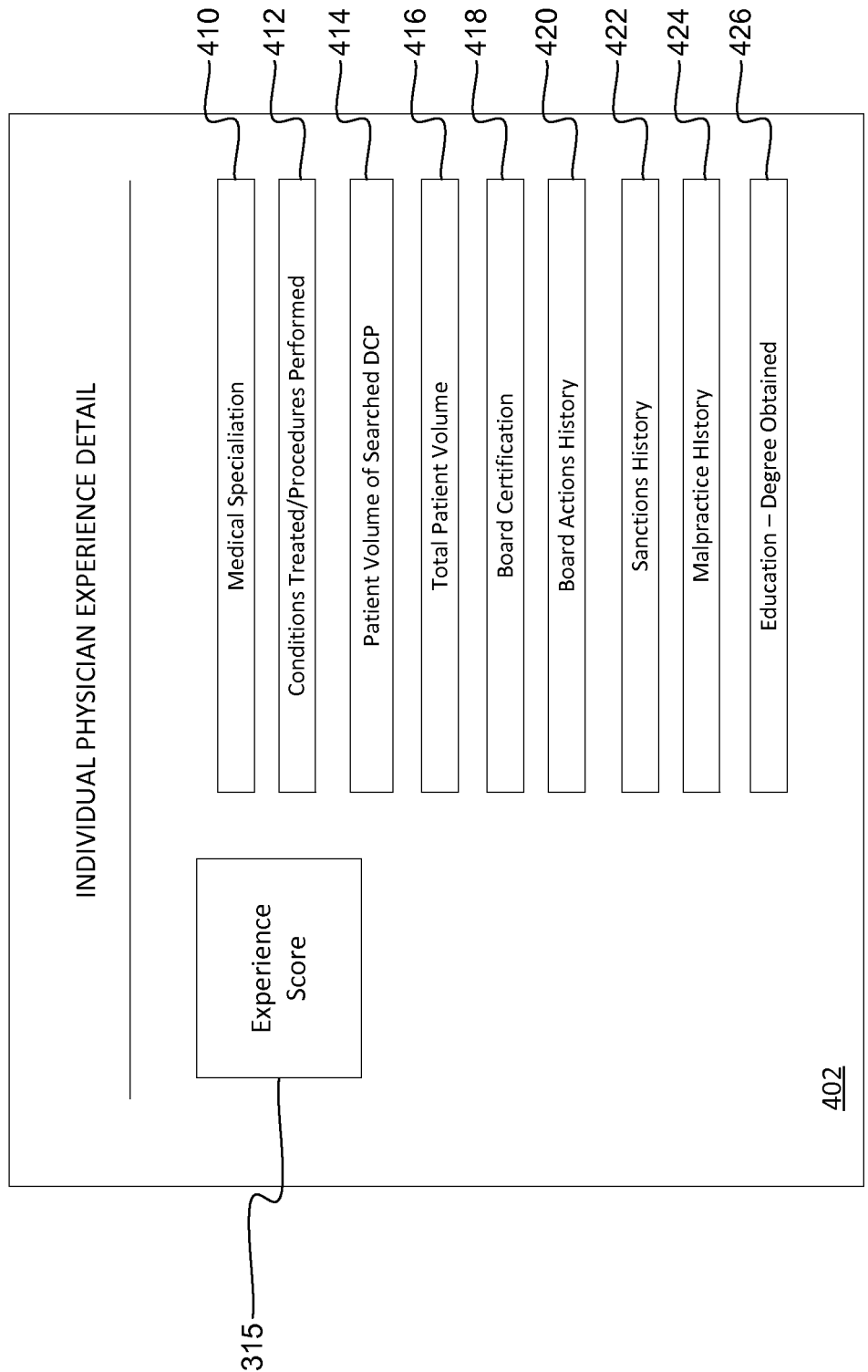
Figure 5:
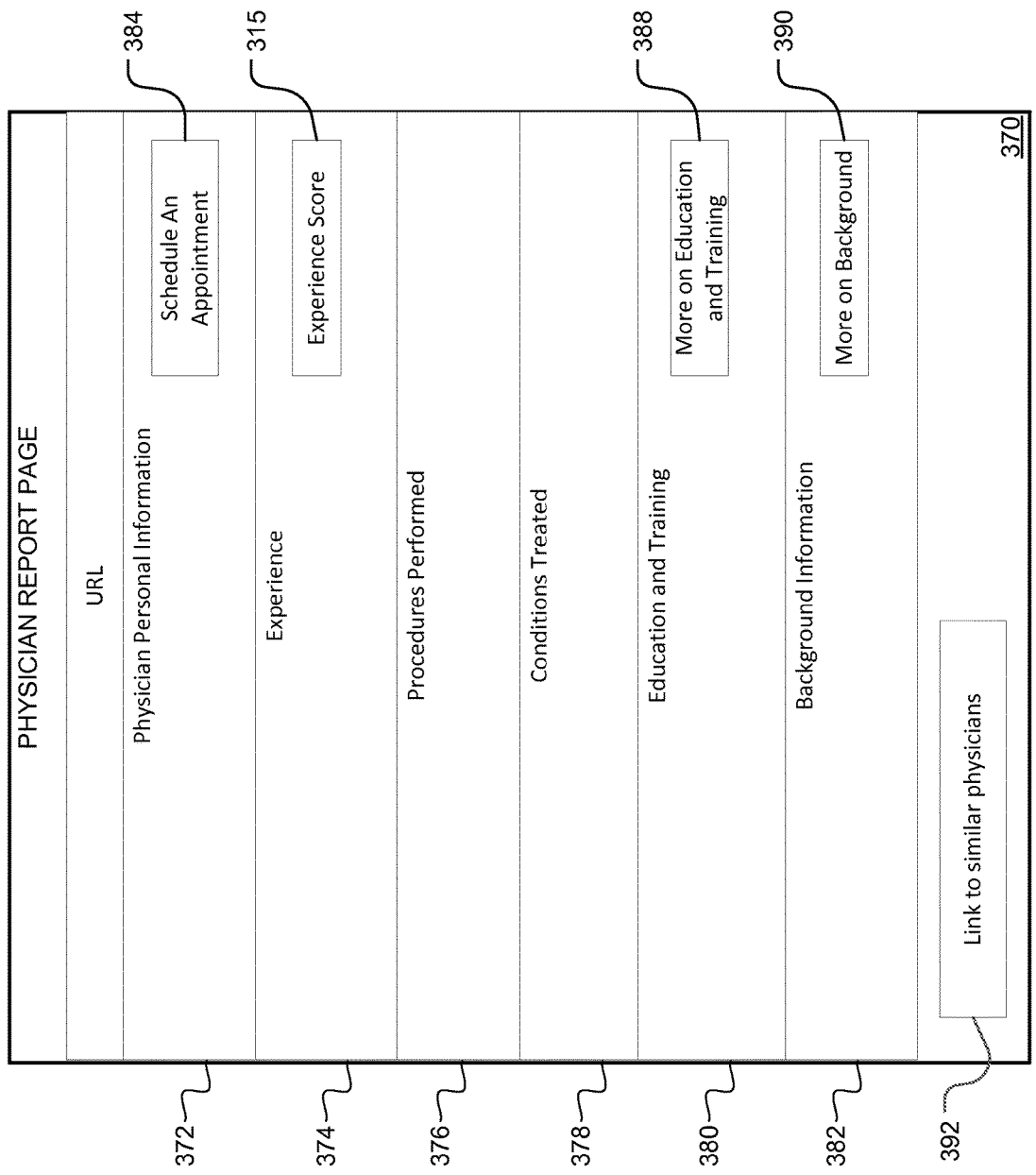

FIG. 3B illustrates the experience score detail page that is accessed from the experience score link 315 from FIG. 3A or FIG. 5.

Figure 4:
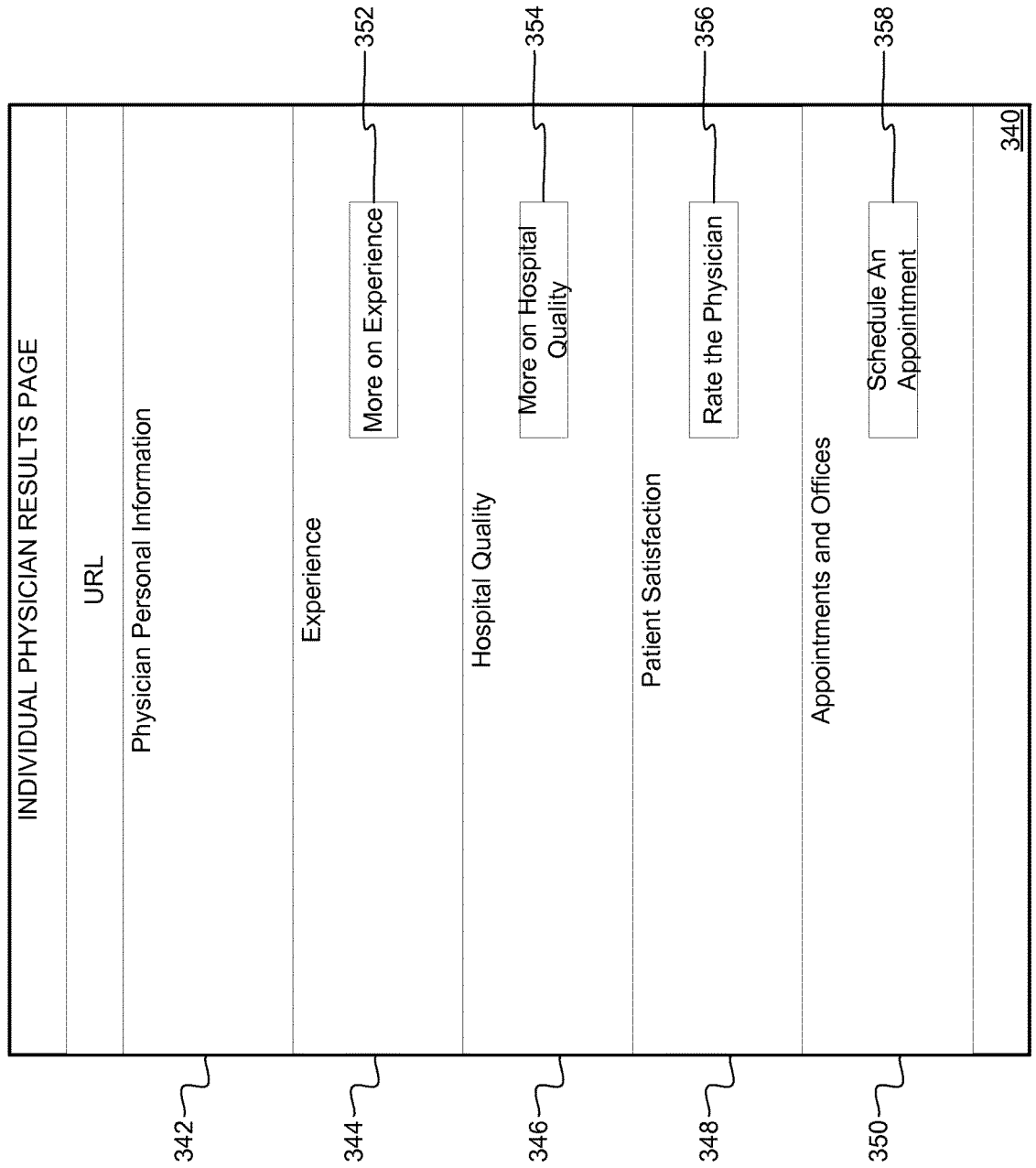

FIG. 4 illustrates search results of a particular physician selected from the search results of FIG. 3, in accordance with an embodiment of the present application.

FIG. 5 illustrates detailed information that may be included in a physician expertise profile, which may be obtained after selecting to view the expertise information in the physician results depicted in FIG. 4, in accordance with an embodiment of the present application.

Figure 6:
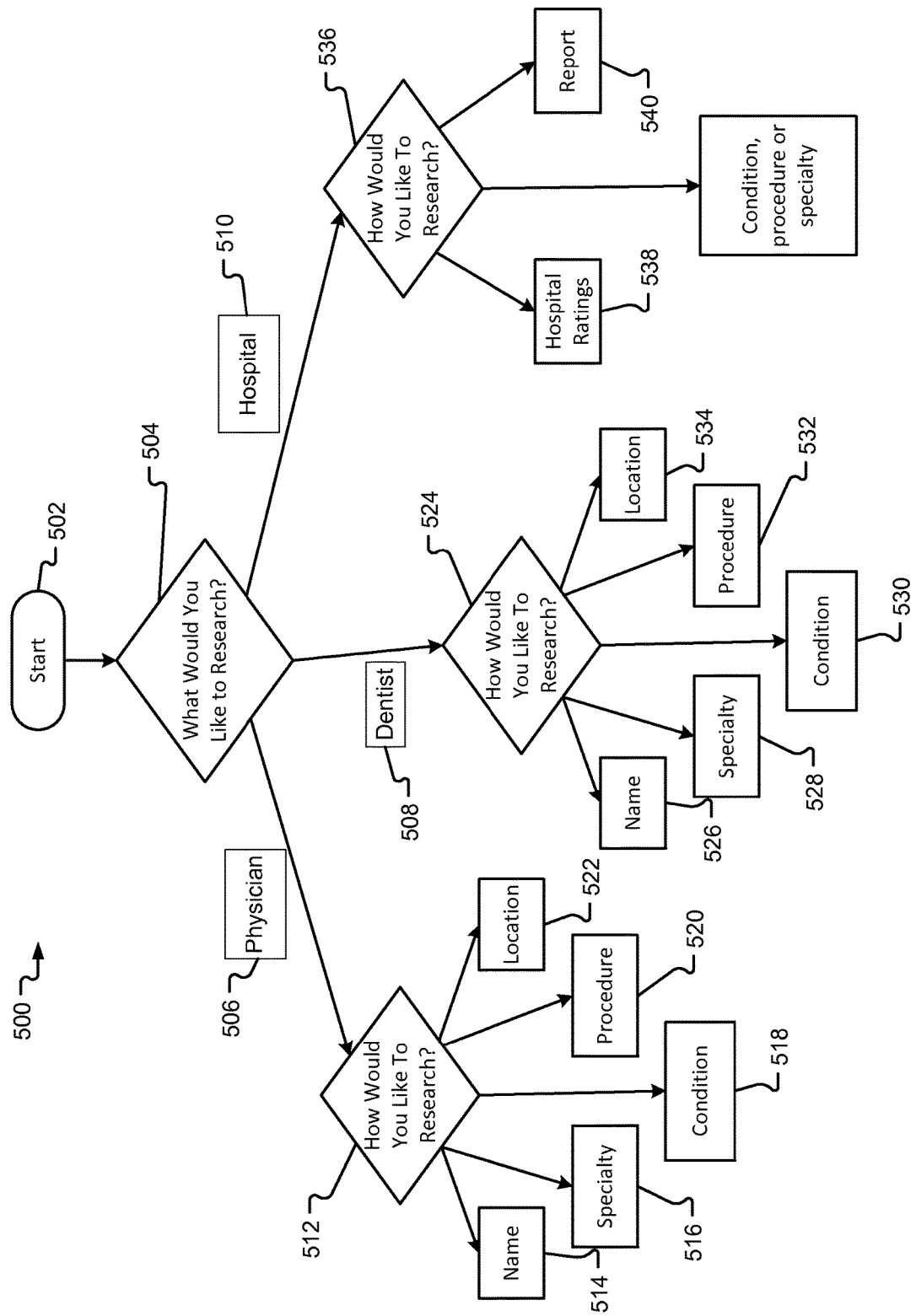

FIG. 6 is a flow diagram illustrating operational characteristics of a search resulting in the search results of FIG. 3, in accordance with an embodiment of the present application.

Figure 7:
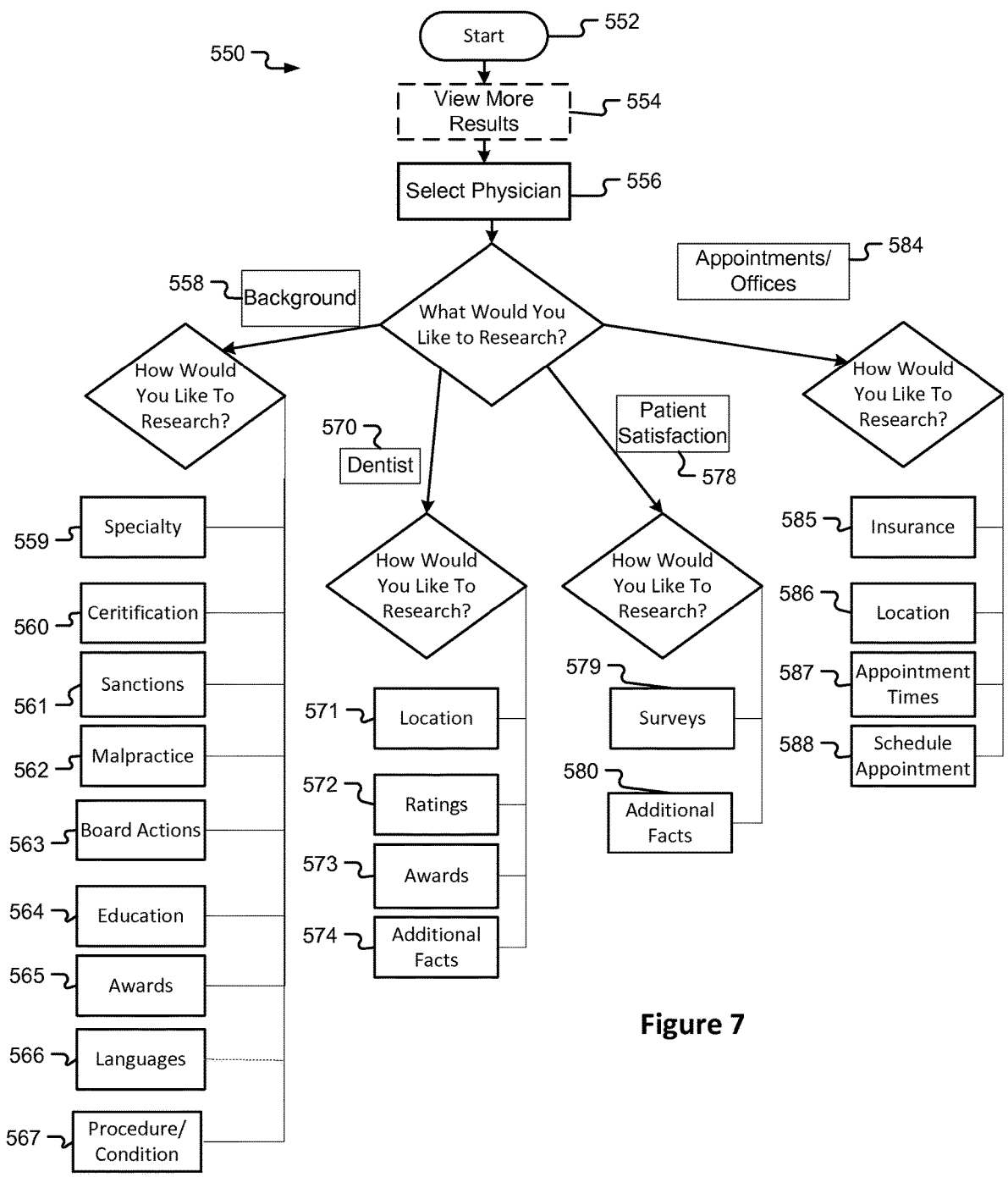

FIG. 7 is a flow diagram illustrating operational characteristics of a search resulting in the search results of FIG. 4, in accordance with an embodiment of the present application.

Figure 8:
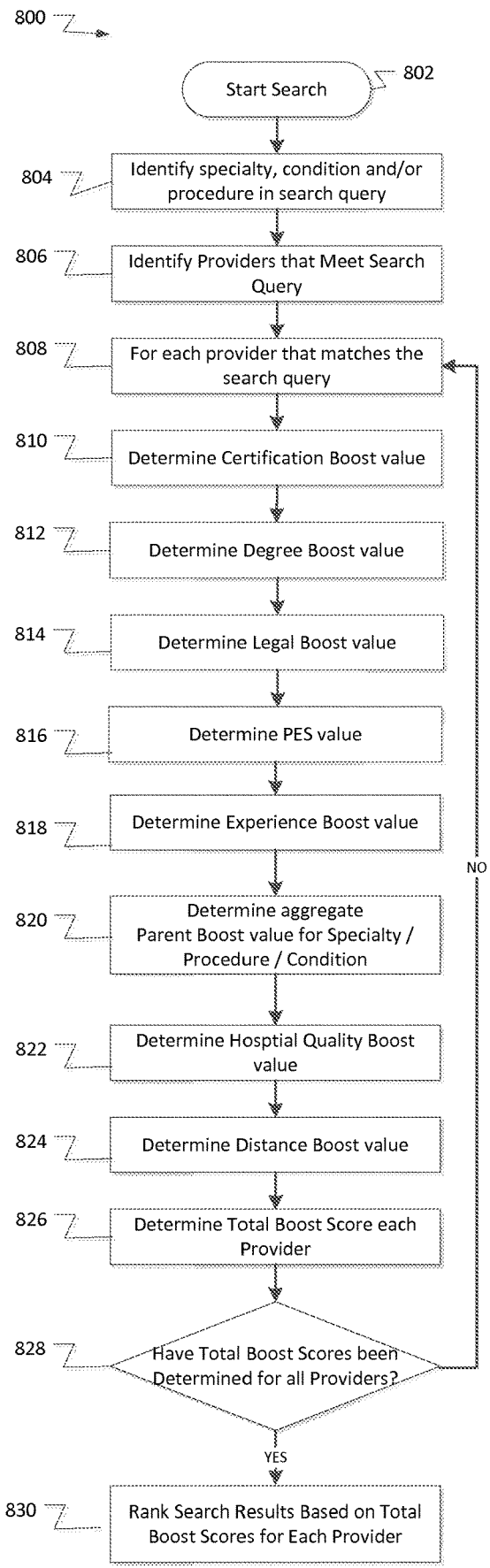

FIG. 8 is a flow diagram illustrating the process 800 for using boost scores to rank search results for a DCP search, in accordance with an embodiment of the present application.

Figure 9:
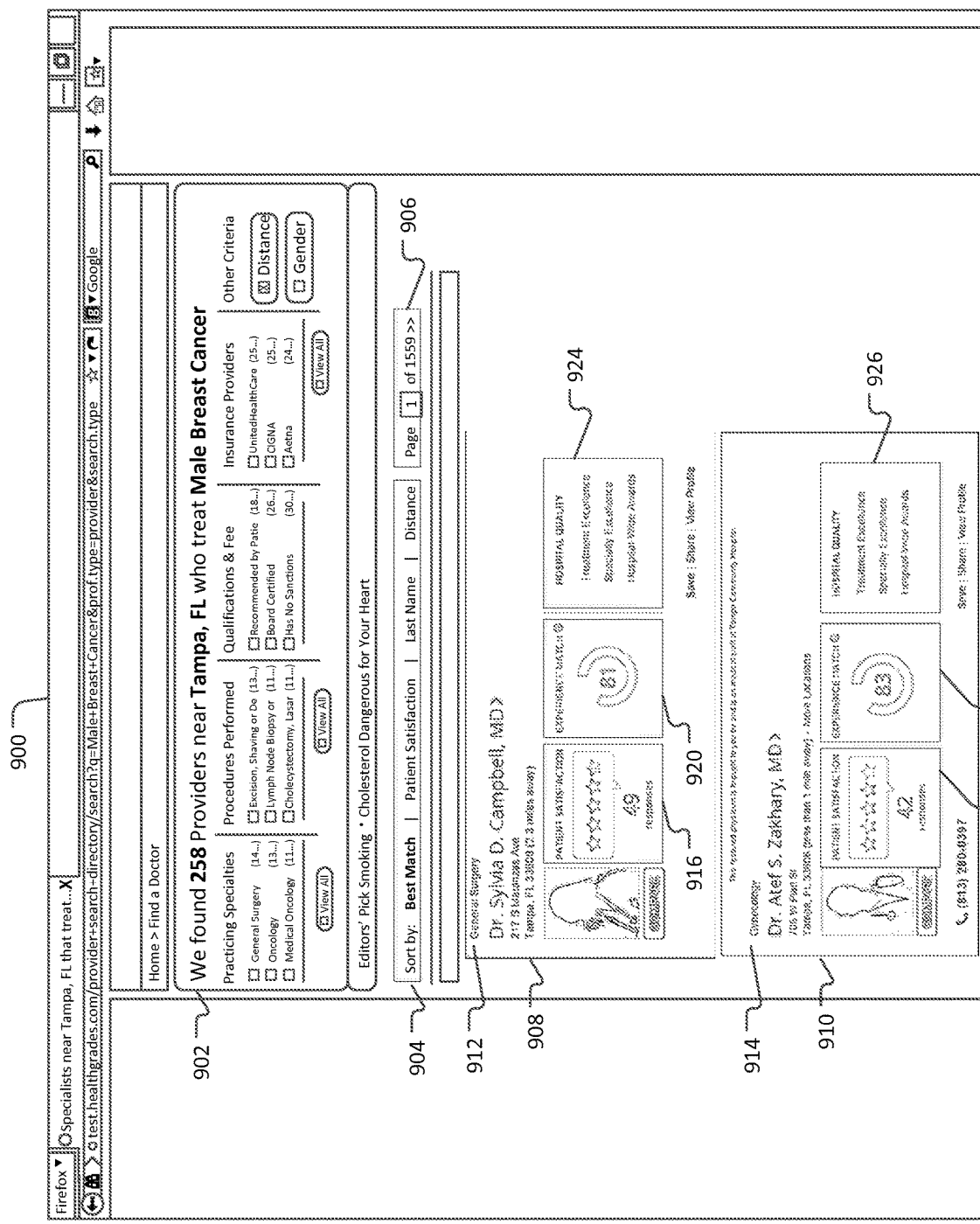

FIG. 9 is a screenshot illustrating search results for a search by "by condition" search using the experience score from FIG. 3B and the total boost score from FIG. 8, in accordance with an embodiment of the present application.

Figure 10:
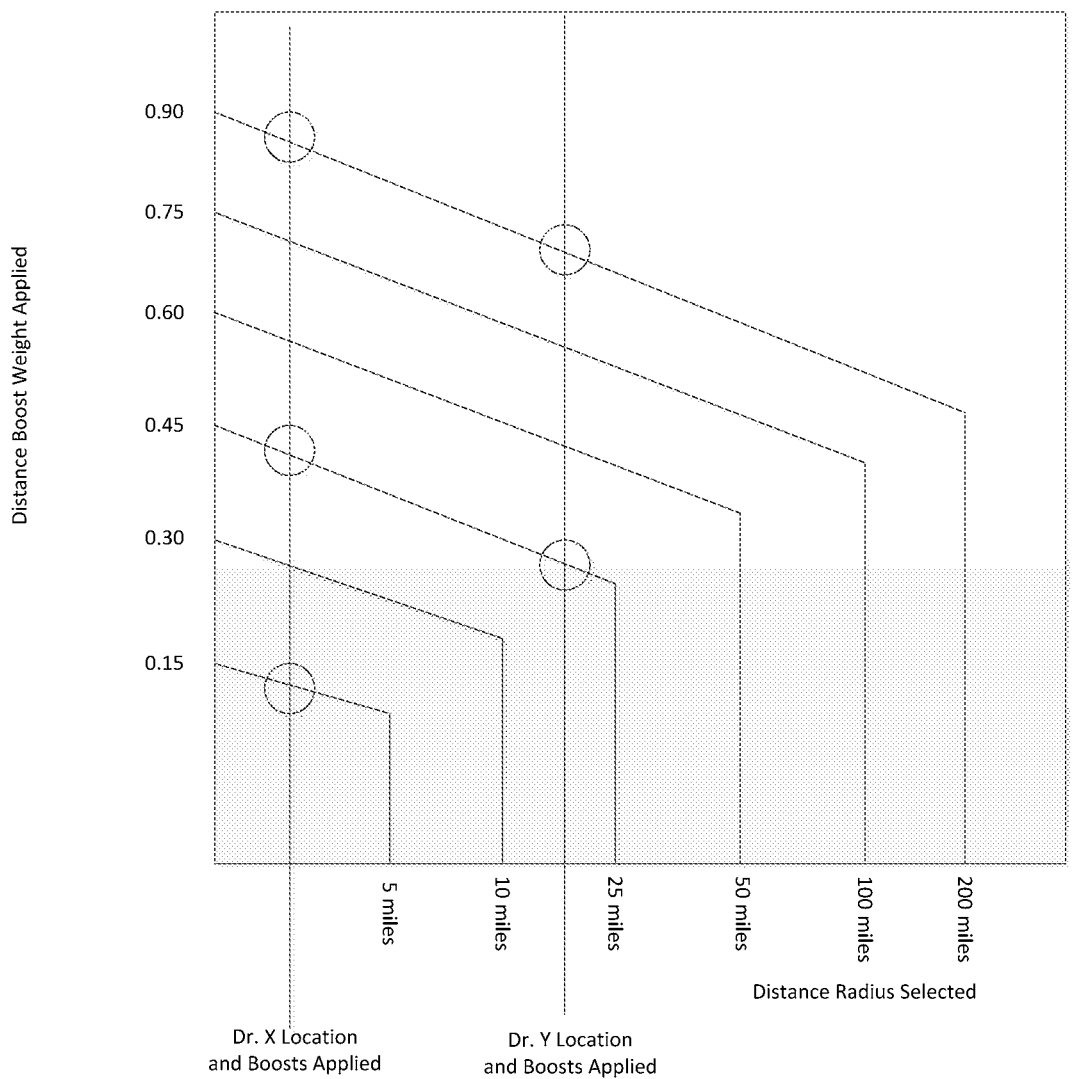

FIG. 10 is a diagram illustrating a relationship between changing the distance radius applied to a specialty search and a distance booth algorithm.

Figure 11:
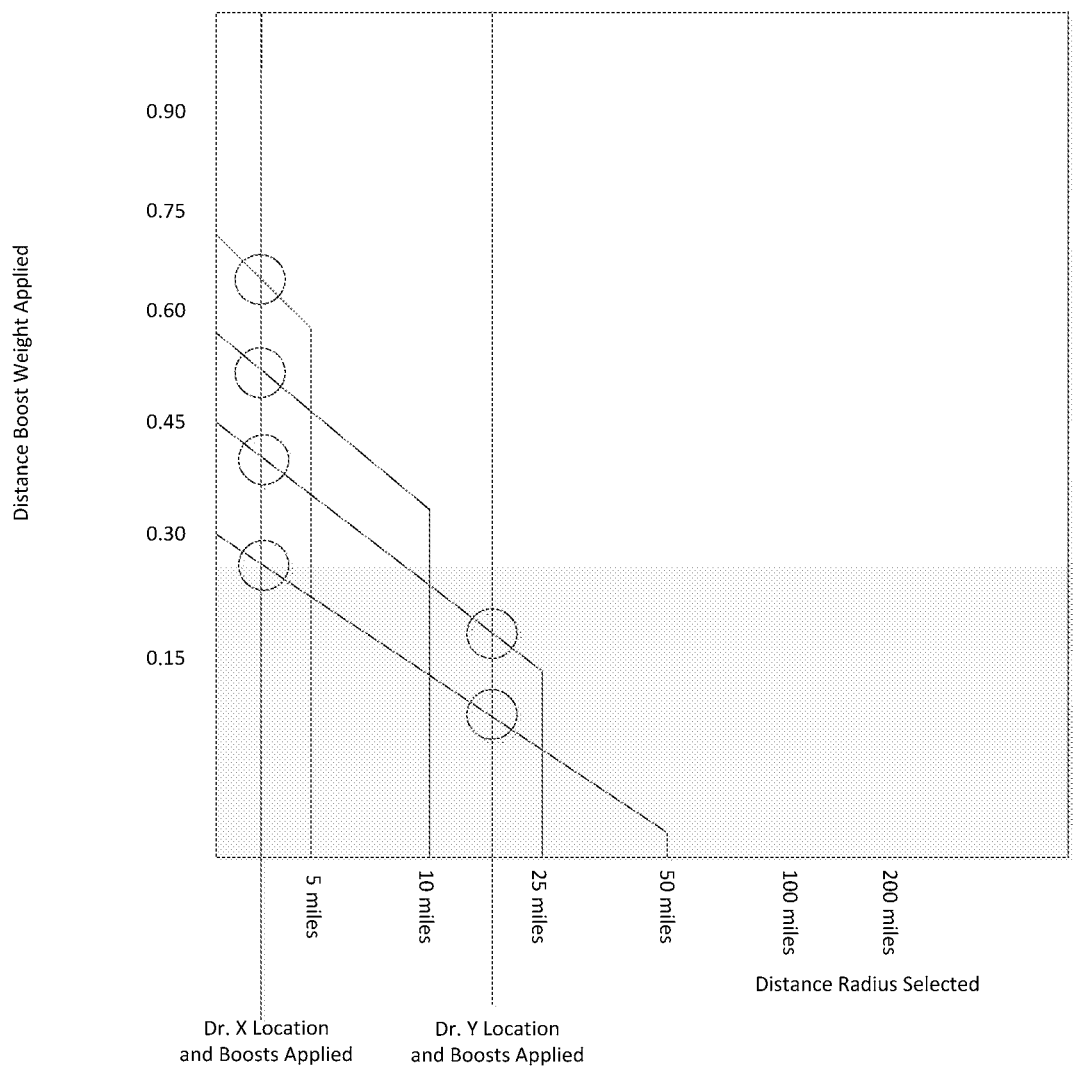

FIG. 11 is a diagram illustrating a relationship between changing the distance radius applied to a DCP search and a distance booth algorithm

DETAILED DESCRIPTION

The disclosure will now describe in detail exemplary embodiments with reference to the accompanying figure, in which the exemplary embodiments are shown. Other aspects may, however, be embodied in many different forms and the inclusion of specific embodiments in this disclosure should not be construed as limiting such aspects to the embodiments set forth herein. Rather, the embodiments depicted in the drawings are included to provide a disclosure that is thorough and complete and which fully conveys the intended scope to those skilled in the art. When referring to the figures, like structures and elements shown throughout are indicated with like reference numerals. Objects depicted in the figures that are covered by another object, as well as the reference annotations thereto, are shown using dashed lines. Optional steps or modules are also shown using dashed lines.

Figure 1:
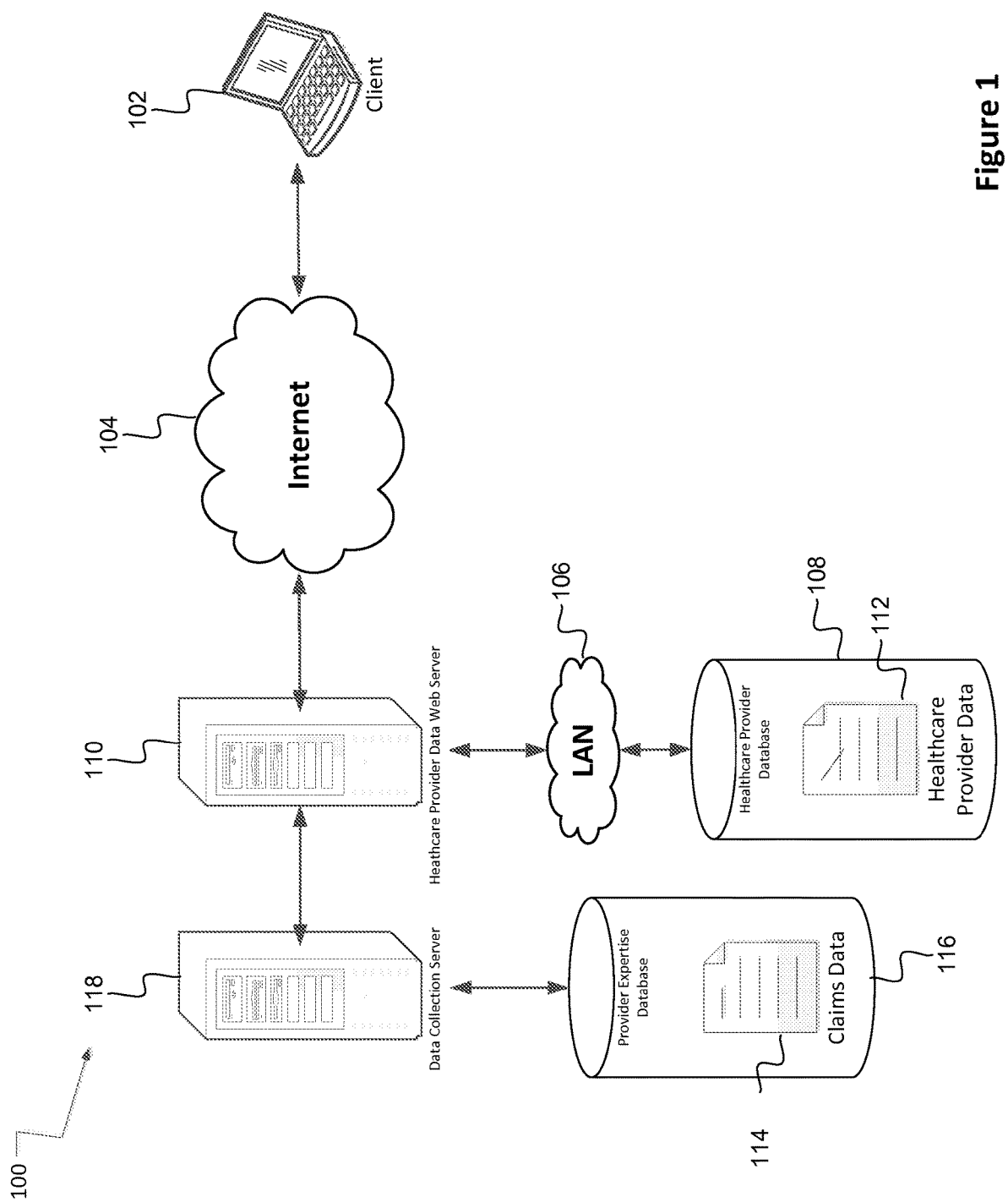
FIG. 1 illustrates a logical representation of a network environment in which users are provided access to the company database containing provider information, wherein the provider information includes claims-related data from an aggregating source, in accordance with an embodiment of the present application.

FIG. 1 illustrates a logical representation of a network environment 100 in which users are provided access to a database containing healthcare provider information. As used herein, the term "healthcare provider" (also referred to simply as "provider") shall mean a human being who provides healthcare services including without limitation doctors, dentists, therapists, physician assistants, nurse practitioners, nurses, chiropractors, and the like. Healthcare providers may make claims on insurance companies for payment or partial payment for conditions treated and/or procedures performed. A "user" is any person using the system 100, typically one seeking healthcare provider information. As such, other terms used to indicate such a user include "consumer," "potential patient," "past patient," "current patient," "referring physician" and/or "patient." In an embodiment, the network environment 100 includes a patient computer 102, a communications network 104, a local area network 106, a database 108 containing healthcare provider information 112, and a web server 110. While only one web server 110 is shown, more than one server computer or separate servers, e.g., a server farm, may be used in accordance with an embodiment of the present invention. Further, although only one patient computer 102 is shown, multiple patient computers could communicate with web server 110. Patient computer 102 may be a desktop computer, a laptop computer, a mobile phone device, a tablet device, or any other devices that may access the network 104 that gives access to websites or applications. In embodiments, the Web server 110, database 108, and healthcare provider information 112 are maintained by the company, although not necessarily so. The network environment 100 is not limited to any particular implementation and instead embodies any computing environment upon which functionality of the environment may be practiced.

The system 100 further involves a backend computer system 118, also referred to as a data collection server 118. The data collection server 118 maintains a database 402 that stores claims data 114. Claims data 114 is the data related to insurance claims submitted for payment or reimbursement from insurance companies by healthcare providers, as discussed in more detail below. In some embodiments, claims data 114 may be used as a measure of patient volumes for conditions and procedures (i.e., measures are not in terms of the number of claims submitted, but the number of patients those claims represent). Also, in other embodiments, healthcare providers may report their own patient volumes for conditions and procedures, in which case claims data 114 would not be the only source for condition and procedure information. In accordance with an embodiment of the present application, a potential patient may simply access the company's webpage 202, which provides the ability to search and retrieve healthcare provider information 112 from the company's database 108, as shown in FIG. 1 to begin a search for a healthcare provider. In such an embodiment, patient computer 102 accesses web server 110 over communications network 104 and receives the webpage 202 of FIG. 2. The exemplary webpage 202 displays search prompts 204, 206 and 208 for a user to research doctors, dentists and/or hospitals, respectively. Although the term "hospitals" is used with respect to exemplary webpage 202, other terms that may be used include clinics, urgent care facilities, dialysis clinics, group practices and/or other treatment facilities. In other embodiments, features of the present application can be implemented in native applications on mobile devices. For instance, application designed for IOS or Android devices may be created to implement the features described and claimed in the present application.

To research a provider according to one embodiment of the present application, a user may select search prompt 204 and use textbox 210 to search the provider by name, area of specialty, conditions treated, procedures performed, or textbox 212 to search by city/state. As used herein, a search by conditions treated or procedures performed will be referred to as a "DCP search." After making the appropriate selection to research a provider, the user may click on "Search" icon 214 to begin the search. In other embodiments, a user may browse into a search listing based upon an index of specialties, procedures and conditions. In such embodiments, no search form is required to gain access to search listings.

In another embodiment, a user may research a dentist by selecting search prompt 206, and using textbox 210 to search the dentist by name, area of specialty, conditions treated, procedures performed, or textbox 212 to search by city/state. After making the appropriate selection to research a dentist, the user may click on Search icon 214 to begin the search. In yet another embodiment, the user may research hospitals by selecting search prompt 208, and using textbox 210 to search a search for free hospital ratings or a hospital profile. To begin the search, the user may click on Search icon 214.

Figure 2:
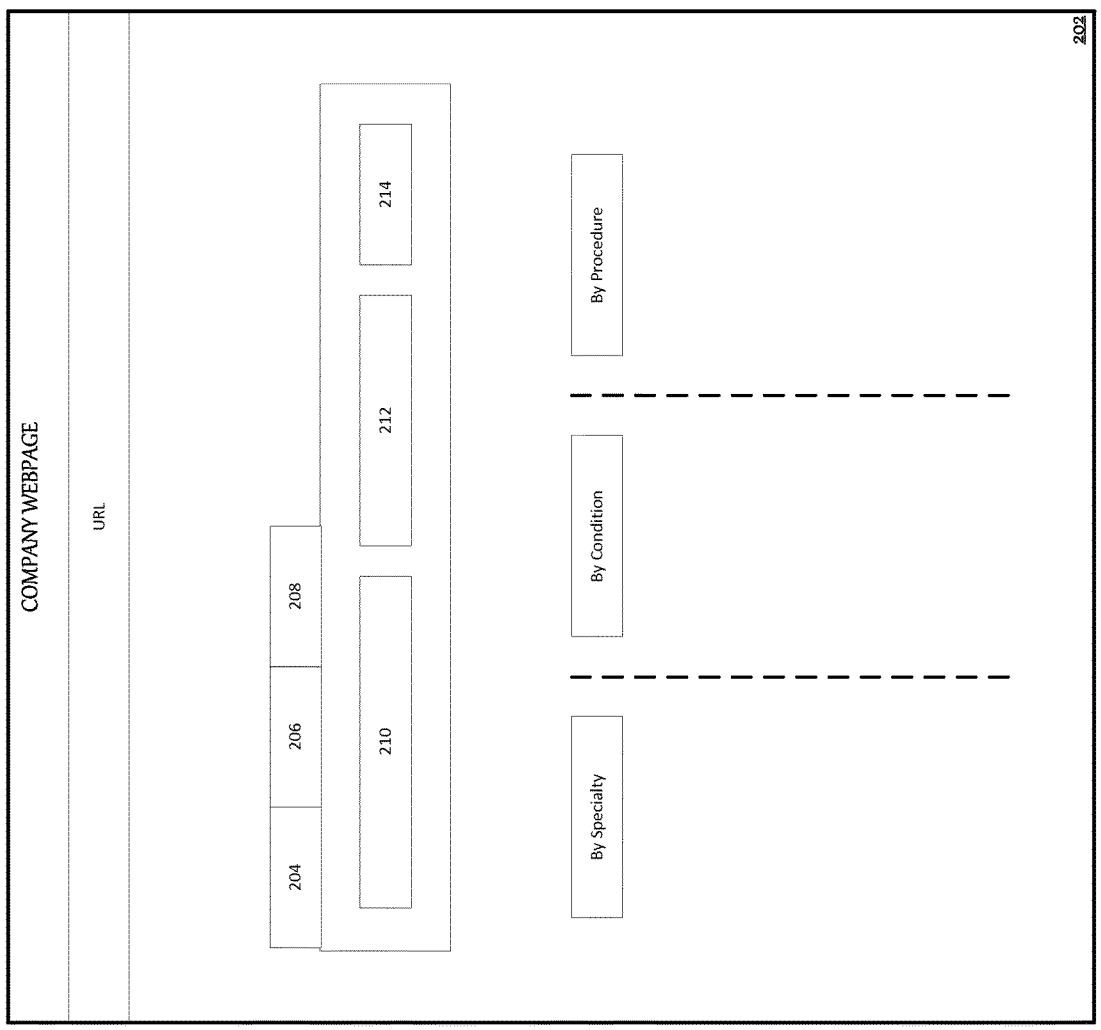
FIG. 2 illustrates a search page on the company website, in accordance with an embodiment of the present application.

In accessing webpage 202 of FIG. 2, patient computer 102 accesses the web server 110 and receives the webpage 202 from the company across a communications network 104. The communications network 104 may be any type of network conventionally known to those skilled in the art. In accordance with an exemplary embodiment, the network may be the global network, e.g., the Internet or World Wide Web. It may also be a local area network or a wide area network. While the network may be any type of network conventionally known to those skilled in the art, the network is described in accordance with an exemplary embodiment as the "World Wide Web." As such, communications over the network occur according to one or more standard packet-based formats, e.g., HTTP, HTTPS, H.323, IP, Ethernet, and/or ATM.

In exemplary embodiments of webpage 202, a user typing within textbox 210 or 212 invokes an autosuggest function. The autosuggest function organizes and displays search terms according to a probabilistic search algorithm. For example, if a user enters "knee" into textbox 210 to research physicians, various "knee"-related results are suggested. These results include "Knee Surgery" in the 'Healthcare Specialty' category, "Knee Arthroscopy" in the 'Procedures They Perform' category; "Knee Sprain" in the 'Conditions They Treat ' category; the physician "Erin Kneedler , PT, Denver, Colo." in the 'Healthcare Providers Near Location' category; and "Knee Foot Ankle Center, Denver, Colo." in the 'Group Practice near Location' category. The user may then highlight or select the desired search term from the autosuggest list. In embodiments, when a user highlights a search term, content associated with the search term may be available for display. For example, highlighting "Knee Arthroscopy" from the above results produces a "What is a Knee Arthroscopy" section that informs the users of the knee arthroscopy procedure. On the other hand, highlighting "Erin Kneedler, PT, Denver, Colo." from the above results produces a brief physician profile section on Erin Kneedler, including links to the results webpage of FIG. 4.

In some embodiments, a location of the user is always part of the search process. For instance, if no search location or search location is provided, one is determined based on last known information about the user or some previous search request. That search location is used in combination with other search criteria to filter the providers that satisfy the search. For example, there may be a default distance radius applied to filter out providers who are located outside of the maximum radius from the search location. Default distance radius values may be set to: 1 mile, 5 miles, 10 miles, 25 miles, 50 miles, 100 miles, 200 miles, 300 miles, 400 miles, 500 miles, 1000 miles, and National. The system dynamically sets the default distance radius value based on different factors including: the specialty, procedure or condition being searched; the rarity of the item being searched; the average fill rates of providers who meet the searched criteria; a corresponding setting applied to the searched term that defines the maximum distance radius that can be applied to the search; and a corresponding setting applied to the searched term that defines the number of providers used to determine the minimum radius from the searched location in which that number of providers who match the searched term must be reached before the radius is selected.

In other embodiments, the radius may be automatically varied based on an initial search result. For instance, in an exemplary embodiment a search may be performed on "Cardiology" in Denver, Colo. Cardiology is set, in this example, to have maximum default distance radius of 100 miles from the searched location and is set to initially locate the first 200 cardiologists closest to the searched the location to identify the minimum radius that may be applied as the default radius to the search. If 200 providers are found within 25 miles of the searched location, the default distance radius is set to 25 miles. If 200 providers are found within 1 mile of the searched location, the default distance radius is set to 1 mile. If the 200 providers are found with 300 miles of the searched location, the default distance radius is set to 100 miles per the maximum default distance radius cap applied to the Cardiology search term. In embodiments, the default distance radius may be expanded or contracted for specific search terms based upon the rarity of the category item being searched and the average fill rates of providers meeting the searched criteria.

Options may be provided to allow the user to broaden their search by location information. For instance, a search may be conducted with a default 100 mile radius from the location given. The user may increase that radius to 250 miles to increase the number of providers that satisfy the search criteria. Alternatively, the user may narrow the search by decreasing the radius to 50 miles, for example.

Turning now to a detailed illustration of the search results obtained after researching a physician as shown and discussed in reference to FIG. 1 and FIG. 2, results for a DCP search by condition treated and geographic location, sometimes referred to as "area code" is shown in FIG. 3. Similar results pages are generated for searches by area of specialty or procedures performed. In an embodiment, a physician search by condition treated and geographic location may produce a results page 302 with a results list 302 of physicians satisfying the search criteria (e.g., condition treated, state, city, and specialty) specified by the user using a best-match ranking algorithm. In other embodiments, the providers are ranked within the results list 302 based on a total boost score, as discussed in more detail below.

In the exemplary embodiment depicted in FIG. 3A, each of the providers listed in results list 302 performs the same procedure (e.g. knee replacements), as illustrated in individual provider sections 306, 308, and 310, respectively and in summary label 312. Where the user requests a search by area of specialty, each of the providers listed in the results list 302 preferably has the same specialty. Where the user requests a search by condition treated, each of the providers listed in the results list 302 preferably treats the condition specified in the search query. Each of provider sections 306, 308, and 310 of the results list 302 include the provider names 314, 316, and 318, each of which is a hyperlink to a result webpage for that particular provider (shown in FIG. 4) or to a report 370 (e.g. profile) on that particular provider (shown in FIG. 5). Provider sections 306, 308, and 310 also include patient satisfaction sections 322, 324, and 326, experience scores 322, 324, and 326, and hospital quality sections 321, 323, and 325.

Patient satisfaction sections 322, 324, and 326 preferably include an average patient rating and a number of patients who have responded to a patient satisfaction survey.

Experience scores 315, 317, and 319 provide information about how much experience each particular provider 314, 316, and 318 has with respect to the specialty, condition, or procedure that was searched. In embodiments, experience scores are dynamically determined for each provider each time a search is run and are based on the type of search that is performed (e.g., search by specialty or search by condition or procedure) and the query terms that are used. As discussed generally above, experience scores are calculated based on a number of experience attributes, each of which has points associated with it. Not all of the attributes are relevant to every particular provider for every particular search. The experience score is calculated by aggregating point values associated with the relevant experience attributes for each search.

FIG. 3B is a detail page or tab 402 about a particular provider's experience score for a particular search and is accessed by clicking the experience score 315 from the results list 302 in FIG. 3A. In other embodiments, detail page 402 may also be included as part of the provider report 370 shown in FIG. 4. Detail page 402 lists one or more of the experience attributes that may be used to determine the experience score 315 for a particular provider (Dr. Jack Eng in this case) shown in provider section 306 of FIG. 3A. These experience attributes include: medical specialization 410, conditions treated or procedures performed 412, patient volume of searched DCP (condition treated or procedure performed) 414, total patient volume 416, board certification 418, board actions history 420, sanctions history 422, malpractice history 424, and degree obtained 426. The points for each relevant attribute are aggregated to form the experience scores 315, 317, and 319. In an embodiment, each attribute has a maximum possible point value and the experience score is derived from a fractional comparison of total points available for the aggregation of attribute points for the relevant attributes vs. actual points achieved by each provider for these same attributes. In an embodiment, the total points available for an experience score for a provider is 100. In other embodiments, certain attributes may be weighted more heavily than others within the aggregation of all attribute points.

The following is a breakdown of each experience attribute and how it may be applied and aggregated to form a total experience score.

The medical specialization attribute 410 considers what medical specialty/specialties the provider practices as compared to the specialty that was searched. Providers who have specialties that match the specialty searched will receive more points for attribute 410 than providers who do not. In an embodiment, if the provider's medical specialty is an exact match to the specialty incorporated into the search (e.g., search is performed on or faceted by orthopedic knee surgery and the provider has stated that they are an orthopedic knee surgeon), the provider will receive the full points possible for attribute 410. If the provider's medical specialty is associated with, but is not an exact match to the medical specialty incorporated into the search (e.g., search is performed on or faceted by orthopedic knee surgery and the provider has not stated that they are an orthopedic knee surgeon, but they have stated that they are an orthopedic surgeon), the provider will not receive any points for this attribute.

The conditions treated/procedures performed attribute 412 considers evidence, if any, that the provider has treated a condition and/or performed a procedure that matches the consumer's search. In an embodiment, the points awarded for this attribute are based on whether the provider has verified the searched DCP and the claims volumes verification status for the searched DCP. For example, there may be six different levels of points a provider may receive for attribute 412 as shown in the table below, where 5x is the maximum amount of points available for this attribute:

| Provider Verification Status for Searched DCP | Claims Volumes Verification Status for Searched DCP | Points for Attribute 412 |
|---|---|---|
| Provider has verified the searched DCP | Claims volumes have verified the searched DCP and volumes are high enough to provide volume comparison metrics for the provider | 5x |
| Provider has verified the searched DCP | Claims volumes have verified the searched DCP but volumes are not high enough to provide volume comparison metrics for the provider | 4x |
| Provider has verified the searched DCP | There are no claims volumes for the searched DCP | 3x |
| Provider has not verified the searched DCP | Claims volumes have verified the searched DCP and volumes are high enough to provide volume comparison metrics for the provider | 2x |
| Provider has not verified the searched DCP | Claims volumes have verified the searched DCP but volumes are not high enough to provide volume comparison metrics for the provider | x |
| Provider has not verified the searched DCP | There are no claims volumes for the searched DCP | 0 |

The patient volume of searched DCP attribute 414 awards points based on the total volume of patients a particular provider has diagnosed, treated, or performed procedures on over a certain period of time (e.g., over the past 12 months) for the particular condition or procedure that is being searched. Like attribute 412, attribute 414 may be based upon medical claims data or may be directly sourced from the provider or their representative. In some embodiments, the higher the patient volume a provider has for the searched condition or procedure, the more points the provider will receive for attribute 414. In another embodiment, if a provider meets a threshold patient volume for conditions diagnosed or procedures performed, he or she gets the maximum points available for attribute 414 and if the provider patient volume is below the threshold, that provider does not receive any points for attribute 414.

The total patient volume attribute 416 awards points based on the total volume of patients a provider has seen over certain period of time, for example the past 12 months. In an embodiment, points are awarded to providers based on a fractional comparison of his or her total patient volume compared with the patient volumes all provider total patient volumes on record with the company. For example, if a provider has patient volumes are higher than a certain number of standard deviations of all provider total patient volumes on record in the database 116 at the time of the search, that provider will receive the maximum points possible for attribute 416. If a provider has patient volumes that fall comparatively within a certain number of standard deviations of all provider total patient volumes on record at the time of the search, the provider receives some points, but less than the maximum possible points for this attribute 416. In one embodiment, this provider would receive points that are scaled in accordance with where their total patient volumes fall within the comparative distribution curve of total volumes discussed above. If the provider has patient volumes below a certain number of standard deviations of all provider total patient volumes on record, the provider would not receive any points for attribute 416.

The board certification attribute 418 provides points for providers who have any type of board certification. If the provider does not have any board certifications stored within the database 112 (FIG. 1), the provider does not receive any points for this attribute.

The board actions history attribute 420 provides points for providers who are free of board actions at the time of the search. Providers with board actions do not receive any points for this attribute.

The sanctions history attribute 422 provides points for providers who are free of sanctions at the time of the search. If the provider does not have any sanctions, the provider will receive the full points possible for this attribute. If the provider does have sanctions stored in the database 112 (FIG. 1), the provider does not receive any points for this attribute.

The malpractice history attribute 424 provides points for providers who have not had any malpractice claims filed against them at the time of the search. If so, they get full points for this attribute. If the provider does have one or more malpractice claims, the provider does not receive points for this attribute.

The education, degree obtained attribute 426 awards points based on the level of education this provider has obtained within their healthcare field of study. In an embodiment, providers with a doctorate level degree (e.g., MD, DO, PhD, etc.) receive the maximum amount of points for attribute 426. Providers with a mid-level degree (e.g. PA) receive some points, but less than the maximum amount of points for this attribute 426. If the provider does not have any medical degrees, the provider does not receive any points for this attribute.

In embodiments, experience scores are dynamically determined for each provider each time a search is run and are based on the type of search that is performed (e.g., search by specialty or search by condition or procedure) and the query terms that are used in each search. So for example, the same particular provider might have one experience score for a search for providers who specialize in orthopedic surgery, a different experience score for search for providers who perform knee replacements, a different experience score for a search for providers who perform steroid injunctions, and still a different experience score for a search for providers who treat carpel tunnel syndrome.

Experience scores are also dynamically determined each time a search is run based on the claims data 114 information that is currently stored in the claims database 116 and the healthcare provider data 112 in database 108 (all shown in FIG. 1). Information within these databases is constantly being updated as providers provide additional information, the company receives additional claims data from insurance companies (e.g. regarding patient volumes, etc.), and third party information is updated. So for example, the same particular provider might have different experience scores for the same search performed at different times is his or her claims volume data has increased or decreased, for example.

Turning back to FIG. 3A, the hospital quality sections 321, 323, and 325 summarize quality ratings and/or scores for hospitals with which the healthcare provider is affiliated. In embodiments, the hospital quality sections may comprise various ratings associated with the provider's affiliated hospital, such as a hospital rating icon, an award icon, a service line icon, and a cohort level icon. In other exemplary embodiments, these rating icons may be located on the result webpage produced by selecting the hyperlinked provider name, such as provider names 314, 316 and 318. In yet other exemplary embodiments, the rating icons may be located on a separate webpage produced by selecting a link on result page 302, such as hyperlinks within sections 321, 323, and 325.

A hospital rating icon may indicate attributes of one or more hospitals associated with the provider. For example, hospital attributes may include information, such as facility's name, address, Top 50 ranking (if available), clinical quality, readmission rates, timeliness of care, patient experience, etc. In certain embodiments, the hospital rating may only reflect ratings associated with one of the hospitals associated with a particular provider. The determination as to which hospital to associate with the provider may include analyzing the percentage and or total of conditions treated or procedures performed, the relevancy of the search term to those percentages and/or totals, the location of the hospital, and/or other information pertinent hospital information. Hospital rating information is helpful to users because there are often significant variations in health outcomes between hospitals within the same community.

An awards icon may indicate awards received by the hospital, such as awards for, patient satisfaction, and key performance measures, such as risk-adjusted mortality, complications and patient safety indices; 30-day mortality and readmission rates; severity-adjusted average length of stay, etc.

A service line icon may indicate information associated with a particular specialty group or wing of a hospital. For example, the service line for a search for "Orthopedic Surgery" may refer to the orthopedic wing/department of the particular hospital associated with the provider. In such an example, the service line icon may contain orthopedic-specific information for the hospital, such as the number of musculoskeletal symptoms and complaints reported, patient satisfaction, average length of stay, readmission statistics, etc.

A cohort level icon may indicate information associated with the particular condition or procedure identified in the search term(s). For example, a search for the condition "Total Knee Replacement" may produce procedure-specific information for patients treated in the particular hospital associated with the provider. Such information may include, the percentage and/or total number of patients treated who have had Total Knee Replacements performed, patient satisfaction, mortality and complication rates, treatment cost estimates, etc.

In an embodiment where the results are too numerous to list on one webpage, a hyperlink 320 to additional providers satisfying the search results, is included. In other embodiments, most if not all the providers satisfying the search results are provided on the same results page. If the user is unable to see some of the providers' information on the page, the user need only scroll down to view the rest. Such layouts of lists are known to those skilled in the art. In an embodiment, for example, multiple pages of results are returned for a single search. In such a case, the number of healthcare providers displayed per page may be limited to a predefined number, such as 20. Additional controls are provided to allow the user to navigate to other pages of results in such a case. Pages are just a way of breaking up the returned listings into consumable views of 20 healthcare providers at a time for the performed search.

In another embodiment, e.g., where a hospital pays a fee to the company, a hyperlink to the hospital affiliated with a particular provider listed, such as hyperlinks 322, 324, and 326, will also be provided under that provider's name. In yet another embodiment, an advertisement 328 for a practice group or hospital or other paying entity may be provided at the top of the results page. This advertisement may be for a practice group or hospital closely related to the search criteria, or, in another embodiment, the advertisement may be for any entity or provider. In an embodiment, the advertisement may contain a hyperlink 330 for providing a report or ratings on that entity.

A user who selects to view a particular provider receives a results webpage 340 containing an overview of information about that particular provider, as depicted in FIG. 4. In an exemplary embodiment, results page 340 contains multiple sections. The provider verified information section 342 contains provider personal information that has been provided by the provider, such as specialty information, gender, age, medical philosophy, years in practice, etc. This information may be provided by the provider and may or may not be verified by an independent third party.

The results webpage 340 may further include an expertise section 344. Expertise section 344 comprises information preferably verified by (e.g. gathered from) an independent third party, such as the company, regarding the provider's actual experience and training, such as board certification(s), licensure(s), and any and/or all malpractice suits and disciplinary actions, both state and federal, to date or within a certain time period. In one embodiment, such verification may be expressly noted in the profile. In essence, the verification of this information provides a user with some assurance that the qualifications of the provider have been checked by someone. In addition to verifications of board certifications and disciplinary actions, an embodiment may include verifications which also relate to the provider's medical school(s), internship, residency, fellowship information, etc. In embodiments, the verification information may also include performance information, such as specialty, number of procedures performed, number of conditions treated, important dates, etc. In yet another embodiment, as discussed below in reference to FIG. 5, the user may click on a hyperlink 352 in this section to access a provider expertise profile as shown in FIGS. 3B and 5.

Exemplary webpage 340 further includes a hospital quality section 346 that comprises information concerning the medical facility (e.g. hospital) with which the provider is affiliated or associated. In one embodiment, this section includes the facility's name, address, rating, awards, sanctions, pertinent facts concerning the facility's quality, and a hyperlink 354 to additional facility information (e.g., the website of the affiliated facility or a Frequently Asked Questions webpage). Such information provides the user with an understanding of the types of medical affiliations the provider has accrued and the locales in which any procedures or treatments may occur.

Exemplary webpage 340 further includes a section 348 that comprises information that relates to patient-provided information and, preferably, relates to information that has been provided by past or current patients of the particular healthcare provider. In one embodiment, patient ratings by current or former patients of the particular provider may be available. This may further include national averages based on certain predetermined questions conducted through surveys. By providing this information, the potential patient can view past performance of a particular doctor through another past or current patient's eyes. In another embodiment related to this section, the user accessing the profile may click on a button 356 to rate the provider if he or she is currently, or has previously been, a patient of that provider (or other healthcare provider). In yet other embodiments, users may rate healthcare providers independent of whether they are actual past or current patients.

Exemplary webpage 340 further includes section 350 which comprises contact information for the provider, which, by way of example only, may include location information, phone numbers, hours of operation, affiliated hospitals, health plans or other insurance information, etc. Additionally, in some embodiments, a hyperlink 358 may be provided to allow the user to directly access an appointment module from the results webpage. The user may set an appointment directly from the appointment module.

While specific sections are shown and discussed in reference to the results webpage, it is conceivable that the results webpage could contain numerous additional sections (while other embodiments may comprise fewer sections). Further, while this disclosure has listed specific types of information and data available in the results webpage in accordance with an embodiment of the present application, other embodiments of the present application may include other types of information and/or data. Moreover, other embodiments may have a different ordering of the sections or different buttons in the sections. The exemplary embodiments depicted and discussed herein are not intended to limit the scope of the present application.

Turning now to FIG. 5, a detailed illustration of physician expertise page 370 obtained after selecting expertise information hyperlink 352 of a researched physician as discussed in reference to FIG. 4, is shown. Although healthcare provider expertise page 370 is referred to as a page herein, it is to be understood that healthcare provider expertise page 370 could be a popup, a tab, a tool tip, etc. The information in physician expertise page 370 may be provided by the physician or the healthcare provider and may or may not be verified by an independent third party. In an exemplary embodiment, physician expertise page 370 contains six sections. The first section 372 contains physician personal information, such as, gender, age, medical philosophy, years in practice, contact information, etc. In embodiments, this section may also contain the experience score information discussed in connection with FIG. 3B and may also contain an appointment module 384 as described above.

The second section 374 comprises an enumerated list of the physician's specialty areas. In embodiments, a physician may elect to report or display less than all of the physician's specialty areas. The determination to under-report specialty area may allow the physician to solicit patients in preferred specialty areas, while maintaining or decreasing the number of patients in less preferred specialty areas. In some embodiments, this may also contain the experience score 315 and the other information shown in FIG. 3B. In other embodiments, statistics relating to the volume of procedures and/or conditions performed in each enumerated specialty area are displayed. Such statistical data provides users with the ability to evaluate which potential physicians may be best suited for the user's specific needs and treatments.

The third section 376 comprises an enumerated list of the procedures actually performed by the physician. In embodiments, a physician may or may not elect to report or display less than all of the performed procedures. In other embodiments, the physician may not have control over the information reported in this section. Statistics relating to the volume of each procedures performed may be displayed with varying degrees of granularity, as discussed below. Similarly, the fourth section 378 comprises an enumerated list of the conditions treated by the physician. In embodiments, a physician may or may not elect to report or display less than all of the conditions treated. Statistics relating to the volume of each conditions treated may be displayed with varying degrees of granularity.

The fifth section 380 comprises information relating to the education and training of the physician, such as medical school, residency and fellowship, among others. In embodiments, this section may also contain a hyperlink 388 to the explanatory details of the information listed in this section.

The sixth section 382 comprises information relating to the background check of the physician. This information may include medical malpractice proceedings, state and federal sanctions, board action, etc. In embodiments, this section may also contain a hyperlink 390 to the explanatory details of the information listed in this section.

In some embodiments, the physician expertise page 370 may also provide a link to other physicians 392 that links to physicians that also satisfy the search criteria. Or, alternatively, link 392 simply links to a results list of similar physicians.

While six sections are shown and discussed in reference to physician expertise page 370, it is conceivable that physician expertise page 370 could contain numerous additional sections. Further, while this disclosure has listed specific types of information and data available in the physician expertise page in accordance with an embodiment of the present application, other embodiments of the present application may include other providers, types of information and/or data. Moreover, other embodiments may have a different ordering of the sections or different buttons in the sections. The exemplary embodiments depicted and discussed herein are not intended to limit the scope of the present application.

Returning to FIG. 1, the data 112 may be acquired by the server 108 from data collection server 118 and may be verified and/or validated by a third party. Claims data 114, also referred to as provider expertise information may include: area(s) of specialty, the total number of patients treated for a condition by a particular healthcare provider, the total number of patients treated for a procedure by the healthcare provider, the volume of patients for a specific condition as a percentage of all conditions treated, the total volume of patients within a provider's practice, and the volume of procedures (on a patient level) as a percentage of all procedures performed. In one embodiment, the company web server 110 may have access to a means to aggregate expertise information about the provider. Such means may include a program, method, routine, etc., such as aggregation routine (not shown), that, when executed by web server 110, causes web server 110 to establish a network connection over communications network 104 to a data collection server 118 containing current provider expertise information 114. In another embodiment, data collection server 118 may establish the network connection to web server 110 based upon a predefined time interval or an on demand request by a user to generate a healthcare provider profile. In such embodiments, the network connection to data collection server 118 may be authenticated by data collection server 118, prior to aggregating requested provider expertise information 114. After aggregating requested provider expertise information 114, the data collection server 118 may transmit to the web server 110 any provider expertise information 114 that has been altered and/or updated since web server 110 last connected to data collection server 118.

In another embodiment, the company may make requests to a third party for provider expertise information 114. The requests may be made in response to analysis by the company regarding provider specialty categories; the frequency distribution of diseases diagnosed/treated, conditions diagnosed/treated, or procedures recommended/performed; or a combination thereof. In such embodiments, the third party may aggregate, and provide to the company, medical claims data regarding in-patient and out-patient procedures, treatments, and/or conditions. In embodiments, the third party supplying the provider expertise information 114 may obtain the medical claims data from institutions providing clearing and settlement services, provider practice management information systems, vendors, and/or hospitals.

When the company receives the provider expertise information 114, the provider expertise information 114 is inserted into, or used to update, the associated records in database 108. In embodiments, received provider expertise information 114 is associated with healthcare provider information and data 112 in database 108 through provider identifiers, such as a National Provider Identifier (NPI). The provider expertise information 114 received by the company may be categorized and aggregated into buckets of data (e.g., groups of ICD-9 codes). In one embodiment, company web server 110 contains the functionality to receive and import the provider expertise information 114 into database 108. In another embodiment, data collection server 118 or another third party not shown provide a file or similar database 116 containing the provider expertise information 114 that may be processed by one or more components in network environment 100 of FIG. 1 before being entered in to the company database. As the technologies and processes involved in importing data into a database are well-known to those in the art, any further explanation as to the accessing databases of the architecture surrounding the implementation of databases is omitted.

In an embodiment where the results are too numerous to list on one webpage, a hyperlink 420 to additional providers satisfying the search results, may be included, as discussed with respect to FIG. 3. In other embodiments, most if not all the providers satisfying the search results are provided on the same results page. In another embodiment, e.g., where a hospital pays a fee to the company, a hyperlink to the hospital affiliated with a particular provider listed, such as hyperlinks 422, 424, and 426, will also be provided under that provider's name. In yet another embodiment, an advertisement 328 for a practice group or hospital or other paying entity may be provided at the top of the results page.

With respect to FIG. 6, a process 500 for researching healthcare provider information, as in FIG. 3, is shown in accordance with an embodiment of the present application. Start operation 502 is initiated following user access of company web server 110 over a communications network 104 and the transmittal of webpage 202 to patient computer 102. From start operation 502, the operation flow of the process proceeds to the query operation 504. Query operation 504 determines whether the user would like to research physicians 506, dentists 508, or hospitals 510. Although the process includes two potential healthcare providers, i.e., physicians and dentists, other healthcare providers could be searched for, and information provided. If the user selects to research physicians 506, flow branches to the physician query operation 512, wherein the physician query operation 512 determines whether the user would like to search for physicians by name 514, specialty 516, conditions treated 518, procedures performed 520 or city/state 522. In an embodiment, location only is a search performed where a user has not specified a specialty, condition, procedure, or provider/group practice name. When a location only search is performed, all providers are returned for the specified location regardless of medical specialization. Otherwise, location may be used as part of any other search to filter the various results to those nearest the determined location.

If the user selects to research dentists 508, flow branches to dentists query operation 524, wherein the dentists query operation 524 determines whether the user would like to research dentists by name 526, specialty 528, conditions treated 530, procedures performed 532 or city/state 534. If the user selects to research hospitals 510, flow branches to the hospital query operation 536, wherein the hospital query operation 536 determines whether the user would like to research hospitals by evaluating ratings 538 of hospitals meeting specified criteria, or by receiving a hospital profile 540. In accordance with other embodiments of the present application, the company web server 110 may provide additional search scenarios and types of healthcare entities for which to search. Examples of such entities may include dialysis centers and group practices.

With respect to FIG. 7, a process 550 for researching healthcare provider information, as in FIG. 4, is shown in accordance with an embodiment of the present application. Start operation 552 is initiated following user receipt of the search results from a search performed on company webpage 202. From start operation 552, a user may either select a healthcare provider 556 or may first view additional results 554, if any are available. Upon selecting a healthcare provider 556, the user will receive additional results related to the selected physician, such as information on the physician's background, the quality of the facilities associated with the physician, patient feedback, and appointments and offices. If the user selects to research the physician's background, flow branches to background query operation 558, wherein background query operation 558 determines whether the user would like to research the physician's specialties 559 (e.g., specialty areas, conditions treated, procedure performed, experience score, etc.), certifications 560, sanctions 561, malpractice complaints 562, board actions 563, education and training 564, awards and recognitions 565, languages spoken 566, or procedure/condition 567. If the user selects to research the quality of the facilities associated with the physician, flow branches to the facility query operation 570, wherein the facility query operation 570 determines whether the user would like to research the facility's location 571, ratings 572, awards 573, or additional facts 574 relating to the quality of the facility. If the user selects to research the feedback from patients on their experience with the physician, flow branches to the feedback query operation 578, wherein the feedback query operation 578 determines whether the user would like to research various patient survey results 579 or facts relating to patient satisfaction surveys 580. If the user selects to research the physician's appointments and offices, flow branches to the offices query operation 584, wherein the offices query operation 584 determines whether the user would like to research the insurances accepted by the physician 585, locations of the physician's offices 586, appointment times 587, or to access an appointment module 588.

In particular embodiments, the system dynamically ranks the healthcare providers returned as a result of a provider search from best providers to worst providers, where the best providers are listed first. Determining which providers are best depends on the type of search run (e.g., DCP search vs. a specialty search), the query terms used, the quality and other characteristics of the providers who meet the search query. More specifically, the providers are rank ordered within sorted search results in accordance with a total boost score based on various measures. The total boost score is a summation of values for boosts (i.e., boost scores) available for the type of search performed in which the provider is listed.

There are various types of boosts, each of which may or may not have a value (positive, negative, or zero) associated with it for any particular provider. The boost values are used to calculate the total boost score for a particular healthcare provider The types of boosts include: a certification boost, a degree boost, a distance boost, a legal boost, a PES ("Patient Experience Satisfaction Score and Survey Volumes") boost, Experience boost, one or more parent boosts, a hospital quality boost, and a practicing specialty term boost.

FIG. 8 is a flowchart illustrating the process 800 for using boost scores to rank search results for a DCP search, such as a search for providers who treat Male Breast Cancer (condition) near Tampa Fla.

Process 800 starts by at step 802 when a search is initiated. Step 804 identifies the specialty, condition, or procedure specified in the search query. This specialty, condition, or procedure will be used to determine the boost score value for one or more of the boosts discussed below. At step 806, the system identifies all of the healthcare providers that meet the query for the search. A total boost score will be identified for each of these providers.

At step 810, the system determines the certification boost for each provider, which boosts the search results rank of a provider if he or she has one or more board certifications. For example, a provider who has at least one board certification may receive a certification boost with a positive value. Providers who do not have a board certification will have a certification boost value of 0. In an embodiment, providers who have multiple board certifications will have a higher certification boost value than providers who have only one board certification. In another embodiment, providers who have a board certification from a board associated with the American Board of Medical Specialties ("ABMS") will have a higher certification boost than providers who have a certification from another board.

At step 812, the system determines the degree boost for each provider, which provides for increasing the search results rank of a provider if he or she has doctorate level degree. In one embodiment, providers with doctorate level degree get a higher degree boost value than providers with a mid-level degree (e.g. PA degree). Providers who do not have any of these degrees will have a degree boost value of 0. In other embodiments, a provider with a PA degree will receive the same degree boost value as providers with other types of degrees.

At step 814, the system determines the legal boost for each provider, which provides for lowering the search results rank of providers who have received malpractice claims, disciplinary actions, or other sanctions. In an embodiment, a provider who has one or more malpractice claims in the past 5 years will have a negative value for the legal boost, as will providers who have any sanctions or any board actions. Providers with no malpractice claims, disciplinary actions, sanctions or board actions will have a legal boost value of 0. In an embodiment, the types of legal boost values are cumulative, so for example, a provider who has a malpractice claim and a sanction would have a total legal boost a larger negative value than a provider who has only a malpractice claim, for example.

At step 816, the system determines the PES (Patient Experience Survey) boost for each provider, which provides for raising the search results rank of providers based on the number of patient experience survey responses they have received and/or the average patient satisfaction rating they have received from patient experience survey responses. In another embodiment, the provider may receive a PES boost if the number of survey responses exceeds a threshold number and/or the average rating for this provider exceeds a threshold rating level.

At step 818, the system determines the experience boost for each provider, which provides for raising the search results rank of providers who have verified (e.g. self-reported) that they have experience in a treating a condition or performing a procedure and the claims data associated with the provider also indicate experience in treating the same condition (or performing the procedure). In embodiments, providers may receive a positive boost value if they have self-reported that they have experience treating searched condition (e.g., male breast cancer) and the claims data confirms that they has this experience. In exemplary embodiments, the experience boost is incorporated into the total boost score based on whether the provider has verified the searched DCP and the claims volumes verification status for the searched DCP. For example, in a user search query for dermabrasion, if 1) a provider has verified the dermabrasion procedure and 2) the claims volumes have verified dermabrasion and the volume of claims are high enough to provide volume comparison metrics for the provider, an Experience boost may be calculated. Alternately, if 1) a provider has not verified the dermabrasion procedure and 2) the claims volumes have verified dermabrasion but the volume of claims are not high enough to provide volume comparison metrics for the provider, a smaller experience boost value may be applied or a value of zero may be applied. In such embodiments, a healthcare provider may also receive a boost for a determination that the reported claims volumes are credible.

In an embodiment, a provider will receive a different Experience boost value for each of the following scenarios:

| Provider Verification Status for Searched DCP | Claims Volumes Verification Status for Searched DCP | Value |
| --- | --- | --- |
| Provider has verified Searched DCP | Claims Volumes have Verified Searched DCP and Volumes are High Enough to Provide Volume Comparison Metrics for the Provider | 5x |
| Provider has verified Searched DCP | Claims Volumes have Verified Searched DCP but Volumes are NOT High Enough to Provide Volume Comparison Metrics for the Provider | 4x |
| Provider has verified Searched DCP | There are no Claims Volumes for the Searched DCP | 3x |
| Provider has NOT verified Searched DCP | Claims Volumes have Verified Searched DCP and Volumes are High Enough to Provide Volume Comparison Metrics for the Provider | 2x |
| Provider has NOT verified Searched DCP | Claims Volumes have Verified Searched DCP but Volumes are NOT High Enough to Provide Volume Comparison Metrics for the Provider | x |
| Provider has NOT verified Searched DCP | There are no Claims Volumes for the Searched DCP | 0 |

At step 820, the system determines one or more Parent boosts for each provider, which provide for raising the search results rank of providers whose expertise information has a parent/child relationship with previously-searched and/or previously-identified specialty, condition, and/or procedure information. In embodiments, if a searched specialty, condition, or procedure (i.e., "DCP") is identified as a child to another DCP for which there is provider verification (e.g., the provider has self-reported this information) and/or claims volumes indicate the provider has experience with the parent DCP, the provider will receive a positive value for a first parent boost. For example, in a user search query for laminectomy, if provider verification and/or claims volumes for lamina procedures (the parent DCP for Laminectomy) are identified, the provider will receive a first parent boost value that is a positive number. The boost value, or some percentage thereof, is then applied to the user's DCP search for child DCP Laminectomy. In another example, if the specialty searched is based on the condition "male breast cancer," the first parent boost may relate to breast cancer generally (e.g., male and female) and a second Parent boost may relate to cancer generally (e.g., all other cancers such as lung cancer, skin cancer, etc.). These additional boosts aid in scoring the relevancy of results returned from an initial search on male breast cancer. In an embodiment, there can be up to five parent/child relationship generations for a searched DCP. Summing the total boosts for each parent/child relationship generate a total composite Parent Boost value for the provider.

At step 822, the system determines the hospital quality boost, which provides for raising the search results rank of providers if they are admitted to or have privileges with a hospital that meets a minimum quality threshold. In embodiments, the value of the hospital boost for each physician may vary based on the ratings and information about affiliated hospitals relative to what is searched. For example, if the search seeks providers who perform knee replacements, a provider who is affiliated with a hospital that is rated very highly for knee replacements (cohort level), or orthopedic surgery (service line level), and/or general (hospital level) may receive a higher positive boost value for the hospital boost than a provider who is not affiliated with such a highly rated hospital. In an embodiment, a provider might receive a negative boost value if he or she is affiliated with a hospital with poor ratings.

At step 824, the system determines the distance boost for each provider, which provides for increasing the search results rank of providers based on the distance between a provider's office location and the consumer's search location factors. In some embodiments, the distance boost value may be varied based on the type of search performed. For example, in the case of specialty searches (e.g., Cardiologists near 123 Main Street, Denver, Colo.), it is important to find a provider in the searched specialty that is closest to the searched location. If all providers are located within a reasonable distance, providers are then differentiated from other providers based on attributes other than distance (e.g., patient satisfaction score). As such, when the returned search results are narrowed to a local market using the distance radius applied to the search listings (e.g., to list providers within 1 mile, 5 miles, 10 miles, etc.), the role of boosting distance in these cases is less significant because all of the providers listed are already within a close proximity, and the values that differentiate one provider from the next in terms of quality of care become more significant (e.g., a consumer is likely to drive an extra five miles to see a provider if that provider has a higher patient satisfaction score than a provider who is close to their searched location).

As the distance radius applied to the search listing expands, however, (e.g., to 25 miles, 50 miles, 100 miles and above), the inverse of this relationship becomes a more likely (e.g., a consumer is less likely to drive 100 miles to a see a provider because that provider has excellent patient satisfaction scores when there are providers closer who have good patient satisfaction scores, but not as high as the provider who is 100 miles away). To accomplish applying a distance boost value that balances the proximity of a provider to a searched location vs. the other attributes that differentiate those providers in terms of quality of care, a sliding distance boost value algorithm is applied that takes into account the distance radius applied to the search listing and its role in determining how the distance boost adjusts to either elevate distance to ensure that local providers are favored over distant providers or elevates differentiating attributes outside of distance because the providers displayed are already favored in terms of being within a local market.

In particular embodiments, a physician specialty search may be performed for physicians specializing in "Dermatology." If no search location was specified, the location of the computing device may be determined, as described above, and a default radius. In this example, however, the expertise of the specializing physician may be significantly less important to the user than the distance to the physician. As such, the statistical weight/value assigned to the distance boost may be high, e.g., 0.7 on a scale of 0.0 to 1.0, compared to other scored values in the search, e.g., certification boost value may be 0.05 and degree boost value may be 0.1, and the default radius may be smaller, e.g., 35 miles. In this example, 100 providers are found within 35 miles of the searched location. Of the 100 providers, 10 providers are located within 5 miles of the searched location, 25 providers are located between 5 and 20 miles of the searched location, and 70 providers are located between 20 and 35 miles of the searched location. In certain embodiments, those providers located within 5 miles of the searched location may receive a relatively high distance boost value, e.g., 0.5, while those providers located outside of the 5 mile search radius receive distance boost values that decrease inversely proportionate to the provider's distance from the searched location. For example, providers located between 5 and 20 miles of the searched location may receive distance boost values of 0.3, while providers located between 20 and 35 miles of the searched location may receive distance boost values of 0.15.

In other embodiments, instead of receiving proportionately diminishing location values for providers located further away from the searched location, the location value is determined by the size of the search radius in relation to the distance of the provider from the searched location. For example, a physician specialty search may be performed for physicians specializing in "Dermatology" within 15 miles of Denver, Colo. In this example, 40 providers are found within 15 miles of the searched location. Of the 40 providers, 5 providers are located within 5 miles of the searched location, 15 providers are located between 5 and 10 miles of the searched location, and 20 providers are located between 10 and 15 miles of the searched location. Although the expertise of the specializing physician may be significantly less important to the user than the distance to the physician, a relatively small search radius has been defined. As such, the statistical weight and/or boost assigned to the location value may be only slightly elevated or even slightly depressed compared to other scored values in the search. In certain embodiments, providers located within 5 miles of the searched location may receive a distance boost value of 0.15, providers located between 5 and 10 miles of the searched location may receive a distance boost value of 0.14 and providers located between 10 and 15 miles of the searched location may receive a distance boost value of 0.13. In another example, the above physician specialty search for physicians specializing in "Dermatology" is extended from within 15 miles of Denver, Colo. to within 100 miles of Denver, Colo. In this example, the same 40 providers are found within 15 miles of the searched location, 100 providers are located between 15 and 50 miles of the searched location, and 250 providers are located between 50 and 100 miles of the searched location. This time, because a relatively large search radius has been defined, the statistical weight and/or boost assigned to the location value may be significantly elevated compared to other scored values in the search. For instance, the 40 providers located within 15 miles of the searched location (previously receiving distance boost between 0.13 and 0.15) may receive a distance boost value of 0.5, providers located between 15 and 50 miles of the searched location may receive a distance boost value of 0.25 and providers located between 50 and 100 miles of the searched location may receive a distance boost value of 0.1. FIG. 10 is a diagram that shows how changing the distance radius applied to a specialty search would affect the distance applied to two doctors within the listings based upon this sliding distance booth algorithm.

In the case of condition or procedure ("DCP") searches (e.g., providers who perform Total Knee Replacements near 123 Main Street, Denver, Colo.), consumers want to find a provider who is most experienced in their specific care needs and are more willing to travel the distance to seek the care they need should local providers not have that same level of experience. In the case of DCP searches, a high Experience boost (discussed above) value is applied for a providers with experience levels in the searched DCP and the distance boost value that is applied becomes a secondary measure applied to refine ordering providers within the search results when providers have close to same experience scores. As the distance radius applied to the search increases, the role of distance as a boost diminishes on a sliding scale. Once the distance radius applied to the search reaches 100 miles or highest, the distance boost value is 0 and it is removed entirely from the total boost score. In this way, the system identifies the most experienced providers for their healthcare needs without having distance obscure those findings.

For instance, in an exemplary embodiment, a DCP search may be performed for physicians performing the procedure "Brainstem Surgery." In this example, because no search location was specified, the search process may use a geographical IP location ("geo-IP") service to identify the geographical location of the computing device being used to perform the search request. The location of the computing device may then be used to determine the centroid of a geographical area, e.g., city or zip code, to be used to perform the DCP search. A default radius may then be defined, e.g., 500 miles. In such an example, the expertise of the physician performing the procedure may be significantly more important to the user than the distance to the physician. As such, the statistical weight and/or boost assigned to the location value may be low, e.g., 0.1 on a scale of 0.0 to 1.0, compared to other scored values in the search, e.g., certification boost value may be 0.25 and degree boost value may be 0.4. In this example, 1,000 providers are found within 500 miles of the searched location. Of the 1,000 providers, 5 providers are located within 10 miles of the searched location, 100 providers are located between 10 and 50 miles of the searched location, and 895 providers are located between 50 and 500 miles of the searched location. In certain embodiments, those providers located within 10 miles of the searched location may receive a relatively low distance boost value, e.g., 0.1, while those providers located outside of the 10 mile search radius receive distance boost values that decrease inversely proportionate to the provider's distance from the searched location. In other embodiments, instead of receiving proportionately diminishing distance boost values, those providers located outside of the 10 mile search radius may uniformly receive a nominal distance boost, e.g., 0.001, or a distance boost value of 0. FIG. 11 is a diagram that shows how changing the distance radius applied to a DCP search would affect the distance applied to two doctors within the listings based upon this sliding distance booth algorithm.

If and when values exist for these different boosts, adding them together provides a total boost score so that the provider can be ranked, i.e., placed in the list of providers that also have some score values. For example, if a provider has a degree boost value of +0.4 and a certification boost value of +0.25, then these two boost scores are added together to give the provider a single total boost score value of +0.65 that is then used to rank order the provider against other providers within the search results. In all cases, a provider's total boost score determines the provider's position within search result rankings for the search performed. The higher the total boost score, the higher the provider will be displayed within the search listings. For example, a provider with total boost score of 2.5 will be deemed more relevant to the search performed and thus will be displayed higher in the listings than provider who has a total boost score of 1.5.

For specialty searches, there may also be a Practicing Specialty term boost for each provider that provides for raising the search results rank of providers if their specialty is an exact match to the medical specialty incorporated into the search terms. For example, if a search is performed on or faceted by orthopedic knee surgery and the provider has stated that they are an Orthopedic Knee Surgeon, that provider will receive a practicing specialty term boost value of greater than 0. If the specialty searched is not an exact match, the practicing specialty term boost value is zero.

Returning now to FIG. 8, in step 826 the system determines a total boost score for each provider based on an aggregation of one or more of the boosts described above. At step 828, the system determines whether a total boost score has been determined for each provider who matches the search results. If it has not, the system proceeds to step 808. If a total boost score has been determined for each provider who matches the search query, the system proceeds to step 830 where the providers are ranked in the search results based on their total boost scores. In a preferred embodiment, providers are ranked by total boost score where the provider with the highest total boost score is ranked first and the provider with the lowest total boost score is ranked last.

In embodiments, specific algorithms employed for each type of boost incorporated into the total boost score and combine various measures relevant to the type of boost and weights or values that govern the importance of that boost as a portion of the total boost score generated. For example, in a search by condition or procedure (DCP), the provider's experience boost may be deemed to be more important in ordering providers within the search results listings than the PES boost and is weighted accordingly within the overall total boost score. Weights applied within each boosting algorithm are flexible and subject to change in order to refine and improve the relevancy of the calculated boost scores.

In such embodiments, these boost algorithm factors are assigned weights and/or scores. The application of weights and/or scores to these factors allows certain results in the results list to be elevated or "boosted" over other results in results list 302 that may have not been boosted or that may have been devalued by applying the boost algorithm. For example, in response to a search for physicians located in Denver, Colo. with an expertise in Knee Arthroscopy, a results list containing two physicians may be produced. The first-ranked physician on the results list may receive the following boosts: Experience boost (e.g., Knee Arthroscopy) +1.5, Degree boost (e.g., MD) +0.4, PES boost +2.5, Distance boost (e.g., User is within 5 miles of physician's office) +4.0. The second-ranked physician on the results list may receive the following boosts: Experience boost (e.g., Knee Arthroscopy) +1.5, Degree boost (e.g., MD) +0.4, PES boost +3.5, Distance boost (e.g., User is within 25 miles of physician's office) +2.0, Sanctions boost (e.g., Physician has received a sanction(s), board action(s) or malpractice claim(s) in the last 5 years) −0.5. In this example, the first-ranked physician receives a total boost score of 8.8, whereas the second-ranked physician receives a total boost score of 6.9. The first-ranked physician is, therefore, better than the second-ranked physician and thus is displayed higher within the results list than the second-ranked physician. The process of boosting may result in a search results order that is sorted alternately to a search results order in which the boost algorithm was not applied.

In more detailed embodiments, the boost algorithm discussed above determines the relevancy of healthcare provider listings by applying multiple factors matched to a consumers search criteria (e.g., medical specialty, procedures the provider has experience performing, conditions the provider has experience treating, etc.). In exemplary embodiments, the combination of expertise information supplied by the healthcare provider, expertise information supplied by a third party, and, optionally, comparison measures using claims volumes, is used to boost healthcare providers within results list 302. In such embodiments, a user may further boost healthcare providers in results list 302 by further refining the expertise information in results list 302. In such embodiments, the boost algorithm for each type of boost that is incorporated into the total boost score may combine various measures that are relevant to the type of boost and weights that govern the importance of that boost as a portion of the total boost score. For example, in a search for physicians, the physician's Experience boost may be deemed more important than the PES boost to physician ranking within the results list. Accordingly, the physician's Experience boost may be more heavily weighted within the total boost score. In embodiments, the weights applied within each boosting algorithm may be flexible, such that the weights may be changed without difficulty in order to refine and improve the relevancy of the calculated boost scores.

In another example, users may be allowed to refine their search to incorporate multiple layers of experience information and then elevate or boost healthcare providers by experience even further within the listings based upon those refinements. For example, searching on Orthopedic Surgeons in Denver, Colo. returns a relevant listing of providers who are identified as being Orthopedic Surgeons. Refining that search to now include Orthopedic Surgeons who have experience performing Knee Replacements not only limits the listings of providers to matching that criteria, but then re-ranks those providers in accordance with the experience level (for example, as a measure of patient volume determined via claims) in performing Knee Replacements. Refining that search even further to include Orthopedic Surgeons who have experience performing Knee Replacement and who have experience with patients in the treatment of Osteoarthritis, again limits listings and re-ranks providers based upon experience.

In an exemplary embodiment, if the total boost score value exceeds a predetermined threshold, the display will include an indication that the provider treats the searched condition. Other embodiments will show whether particular providers perform specific procedures, e.g., the procedure for which the user initially searched.

In other embodiments, information may be suppressed from, or devalued in, a provider's profile when the boost algorithm is invoked. For example, a heart surgeon may have operated on a patient having other, non-related conditions, such as diabetes. Consequently, the patient will be diagnosed as having a pulmonary condition and a diabetic condition. In such a case, the provider performing the heart surgery may be incorrectly reported as treating both condition categories (pulmonary and diabetic). Therefore any statistical information gathered from the heart surgery that would contribute to associating the provider with treating diabetic conditions may be suppressed or devalued. Such a process may serve to make the data in the provider profiles more accessible to users who may not have extensive medical knowledge or may not be familiar with medical reporting procedures.

FIG. 9 is a results page 900 of a preferred embodiment of the present invention and illustrates a screenshot from a DCP search for providers who treat male breast cancer and are located near Tampa, Fla. Banner 902 summarizes the search query that was used for this search. The search results 900 may be sorted in different ways using the sort button in section 904. The "best match" option sorts the search results by the total boost score as described in connection with FIG. 8. FIG. 9 shows the first page of the search results, additional pages may be viewed by selecting the page navigation hyperlink 906. The two highest ranked providers are shown in FIG. 9. Each provider has his or her own section 908 and 910 of the results list. Each provider section 908 and 910 may include various types of information such as specialty information 912 and 914, patient satisfaction information 916 and 918, an experience score 920 and 922, and hospital quality information 924 and 926, as was described in connection with FIG. 3A. It will be appreciated that although the first healthcare provider (Dr. Sylvia Campbell) has a lower experience score (81) than the second healthcare provider (Dr. Atef Zakhary) (83), Dr. Campbell is listed first because she has a higher total boost score than Dr. Zakhary. While total boost scores may be based in part on similar factors to experience scores, the total boost score may also be based on factors that are not considered for experience scores including, for example, distance and hospital quality.

Having described the embodiments of the present invention with reference to the figures above, it should be appreciated that numerous modifications may be made to the present invention that will readily suggest themselves to those skilled in the art and which are encompassed in the spirit of the invention disclosed and as defined in the appended claims. Indeed, while presently preferred embodiments have been described for purposes of this disclosure, various changes and modifications may be made which are well within the scope of the embodiments presented herein. For example, the present embodiments may not be limited specifically to healthcare provider information but, instead, may be applicable to any kind of professionals, such as engineers, accountants, veterinarians, dentists, etc. Additionally, the inclusion of specific operations and the order of operations shown in the flow diagrams illustrated in FIGS. 6, 7 and 8 are provided for illustrative purposes only and, in accordance with other embodiments, steps may be removed, reordered, modified, or performed simultaneously. Furthermore, it should be appreciated that the scope of the present embodiments accommodates other operations that may be added or removed depending on the needs of the particular entity or entities implementing or using the system.

Similarly, although this disclosure has used language specific to structural features, methodological acts, and computer-readable media containing such acts, it is to be understood that the present invention defined in the appended claims is not necessarily limited to the specific structure, acts, or media described herein. The specific structure, acts, or media are disclosed as exemplary embodiments of implementing the claimed invention. The invention is defined by the appended claims.

What is claimed is:

1. A system for identifying healthcare providers, the system comprising:
 a processing unit; and
 a memory coupled to the processing unit, the memory encoding computer executable instructions that, when executed by the processing unit, perform a method comprising:
 receiving a request to search for one or more of the healthcare providers, wherein the request includes a search query;
 assigning a total boost score to each of the one or more healthcare providers who match the search query, wherein the total boost score is based on an experience boost and one or more values from a group comprising: a certification boost, a degree boost, a distance boost, a legal boost, a parent boost, an affiliated hospital boost, and a practicing specialty term boost;

wherein the experience boost is based on claims information received from a plurality of insurance companies regarding each of the one or more healthcare providers who match the search query and the claims information includes procedure volume information;
ranking the one or more healthcare providers who match the search query based on the total boost score to create a ranked results list; and
providing access to the ranked results list over a computer network.

2. The system defined in claim 1, wherein the request to search for one or more of the healthcare providers further comprises a type of search from a group consisting of: name, specialty, location, diagnosis, conditions treated, and procedures performed.

3. The system defined in claim 2, wherein the total boost score assigned for each of the one or more healthcare providers who match the search query is based in part on the type of search.

4. The system defined in claim 2, further comprising:
determining a search location for the request to search for one or more of the healthcare providers; and
defining a search radius value from the search location based on the type of search.

5. The system defined in claim 4, wherein the total boost score for each of the one or more healthcare providers is based on a distance boost and the distance boost for each of the one or more healthcare providers is based on the type of search.

6. The system defined in claim 4, wherein the total boost score for each of the one or more healthcare providers is based on a distance boost and the distance boost is based on a comparison of a provider location of each of the one or more healthcare providers who match the search query and the search radius value from the search location.

7. The system defined in claim 1, wherein the experience boost and the experience boost is further based on self-reported information received from each of the one or more healthcare providers who match the search query, wherein the self-reported information comprises conditions treated information.

8. The system defined in claim 1, wherein the experience boost is further based on claims information received from one or more insurance companies regarding each of the one or more healthcare providers who match the search query and wherein the claims information further includes conditions treated information.

9. A system for identifying healthcare providers, the system comprising:
a processing unit; and
a memory coupled to the processing unit, the memory encoding computer executable instructions that, when executed by the processing unit, perform a method comprising:
receiving a request to search for one or more of the healthcare providers, wherein the request includes a search query;
assigning a total boost score to each of the one or more healthcare providers who match the search query, wherein the total boost score is based on all of the following: a certification boost, a degree boost, a distance boost, a legal boost, an experience boost, and an affiliated hospital boost;
ranking the one or more healthcare providers who match the search query based on the total boost score to create a ranked results list; and
providing access to the ranked results list over a computer network.

10. A computer-implemented method of providing healthcare provider information to users, said method comprising:
receiving, by a server comprising at least one computer processor and memory, a request to search for one or more of the healthcare providers, wherein the request includes a search query with a search term;
creating an experience score for each of the one or more healthcare providers who match the search query, wherein the experience score is based on the search query and one or more attributes from a group comprising: a medical specialty, a condition treated, a procedure volume, a patient volume for the search term, a total patient volume, a board certification, a board actions history, a sanctions history, a malpractice history, and a level of degree;
wherein the procedure volume attribute relates to one more or procedures and is based on claims data received from a plurality of insurance companies, and wherein the claims data comprises a total number of patients who received the one or more procedures performed by each of the one or more healthcare providers;
aggregating information regarding the procedure volume attribute from the plurality of insurance companies;
creating a search results list using the experience score and the aggregated procedure volume information for each of the one or more healthcare providers who match the search query; and
providing access to the search results list over a computer network.

11. The method as defined in claim 10, wherein the search results list includes a hyperlink to a report on an affiliated hospital, medical center, or other type of treatment center for each of the one or more healthcare providers.

12. The method as defined in claim 10, wherein disciplinary action attribute indicates that the healthcare provider has not received any disciplinary actions.

13. The method as defined in claim 10 further comprising: creating a healthcare provider profile using the experience score for each of the one or more healthcare providers who match the search query.

* * * * *